(12) United States Patent
Beachy

(10) Patent No.: US 6,942,988 B2
(45) Date of Patent: Sep. 13, 2005

(54) METHOD OF USE OF SONIC HEDGEHOG PROTEIN AS A LIGAND FOR PATCHED

(75) Inventor: Philip A. Beachy, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 38 days.

(21) Appl. No.: 09/969,520

(22) Filed: Sep. 24, 2001

(65) Prior Publication Data

US 2002/0177163 A1 Nov. 28, 2002

Related U.S. Application Data

(60) Provisional application No. 60/235,153, filed on Sep. 22, 2000.

(51) Int. Cl.[7] ................................................ C12Q 1/02
(52) U.S. Cl. ........................................................ 435/29
(58) Field of Search ................................ 435/6, 7.8, 29

(56) References Cited

U.S. PATENT DOCUMENTS

| | | | |
|---|---|---|---|
| 5,789,543 | A | 8/1998 | Ingham et al. |
| 6,001,575 | A | 12/1999 | Huganir |
| 6,004,808 | A | 12/1999 | Negulescu et al. |
| 6,261,786 | B1 * | 7/2001 | Marigo et al. |
| 6,281,332 | B1 | 8/2001 | Beachy |
| 6,566,092 | B1 * | 5/2003 | Jessell et al. |

FOREIGN PATENT DOCUMENTS

| | | |
|---|---|---|
| EP | 0 020 029 A1 | 12/1980 |
| WO | WO 96/16668 | 6/1996 |
| WO | WO 98/30576 * | 7/1998 |

OTHER PUBLICATIONS

Williams et al, Journal of Cell Science, Nov. 17, 1999, vol. 112, pp. 4405–4414.*

Baker et al., "Competence, Specification and Induction of Pax–3 in the Trigeminal Placode,"*Development*, 126:147–156, The Company of Biologists Limited 1998 (1999).

Beachy et al., "Multiple Roles of Cholesterol in Hedgehog Protein Biogenesis and Signaling,"*Cold Spring Harbor Symposia on Quantitative Biology*, LXII:191–203, Cold Spring Harbor Laboratory Press (1997).

Bellaiche et al., "*Tout–velu* is a *Drosophila*Homologue of the Putative Tumour Suppressor *EXT–1* and Is Needed for Hh Diffusion,"*Nature*, 394:85–88, Macmillan Publishers Ltd 1998 (1998).

Huber et al., "The Transient Receptor Potential Protein (Trp), a Putative Stored–Operated $Ca^{2+}$Channel Essential for Phosphoinositide–Mediated Photoreception, Forms a Signaling Complex with NorpA, InaC and InaD,", *The EMBO Journal*, 15(24):7036–7045, Oxford University Press (1996).

Lange and Steck, "Cholesterol Homeostasis,"*The Journal of Biological Chemistry*, 269(47) 29371–29374, The American Society for Biochemistry and Molecular Biology, Inc. (1994).

Lee et al., "Autoproteolysis in *hedgehog*Protein Biogenesis, "*Science*, 266(5190): 1528–1537 (1994).

Lee et al., "Secretion and Localized Transcription Suggest a Role in Positional Signaling for Products of the Segmentation Gene *hedgehog*, "*Cell*, 71:33–50, Cell Press (1992).

Lind et al., "The Putatuve Tumor Suppressor EXT1 and EXT2 Are Glycosyltransferases Required for the Biosynthesis of Heparan Sulfate,"*The Journal of Biological Chemistry*, 273(41):26265–26268, The American Society for Biochemistry and Molecular Biology, Inc. (1998).

Marigo and Tabin, "Regulation of *Patched*by Sonic Hedgehog in the Developing Neural Tube,"*Proc. Natl. Acad. Sci.*USA, 93:9346–9351 (1996).

McCormick et al., "The Putative Tumour Suppressor EXT1 Alters the Expression of Cell–Surface Heparan Sulfate, "*Nature Genetics*, 19:158–161, Nature America Inc. (998).

Pepinsky et al., "Identification of a Palmitic Acid–Modified Form of Human Sonic Hedgehog,"*The Journal of Biological Chemistry*, 273(22): 14037–14045, The American Society for Biochemistry and Molecular Biology, Inc. (1998).

Pepinsky et al., "Mapping Sonic Hedgehog–Receptor Interactions by Steric Interference,"*The Journal of Biological Chemistry*, 275(15):10995–11001, The American Society for Biochemistry and Molecular Biology, Inc. (2000).

Porter et al., "Cholesterol Modification of Hedgehog Signaling Proteins in Animal Development,"*Science*, 274:255–259, Nature America Inc. (1996).

Porter et al., "The Product of *hedgehog*Autoproteolytic Cleavage Active in Local and Long–Range Signalling,"*Nature*, 374:363–366 (1995).

* cited by examiner

*Primary Examiner*—Terry McKelvey
(74) *Attorney, Agent, or Firm*—DLA Piper Rudnick Gray Cary US LLP

(57) ABSTRACT

The invention relates to hedgehog proteins that are involved in signaling developmental processes. The proteins of the invention modulate differentiation of neural plate. Also provided are methods for identifying compounds that modulate early events in development and more particularly to methods to identify compounds that modulate differentiation of neural plate using hedgehog proteins as ligands for the patched receptor.

13 Claims, 5 Drawing Sheets

```
mSHH 100 TQRCKDKLNALAISVMNQWPGV KLRVTEGWDE. 131
DD-C 112 ALVTMWKLQAMRHAMG...d.kPIT VNGGFRSv 140

SD         HA SD                 SC   SC
mSHH 132 .DG...HHSEESLHYEGRAVDITTSDRDRSKYG 160
DD-C 141 tcnsnvgGASNSRHMYGHAADLGAGsq...GFC 170

EA SC
mSHH 161 MLARLAVEAGFDWVYY.....ESKAHIHCSVK 187
DD-C 171 ALAQAARNHGFTEILGpgypgH.NDHTHVAGG 201
```

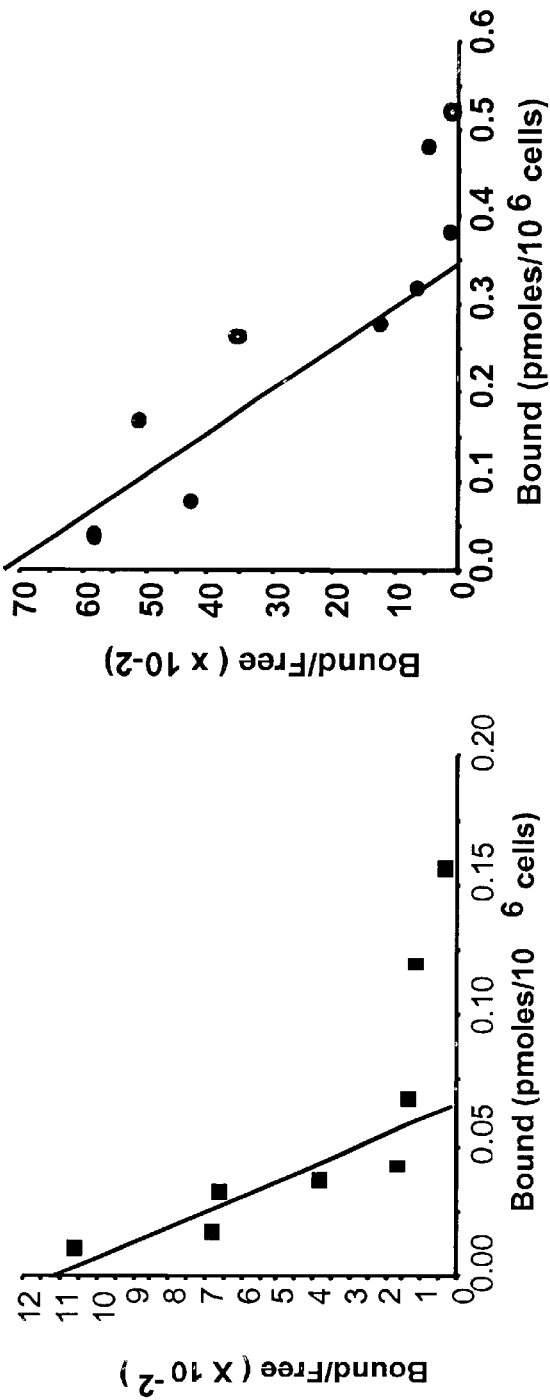

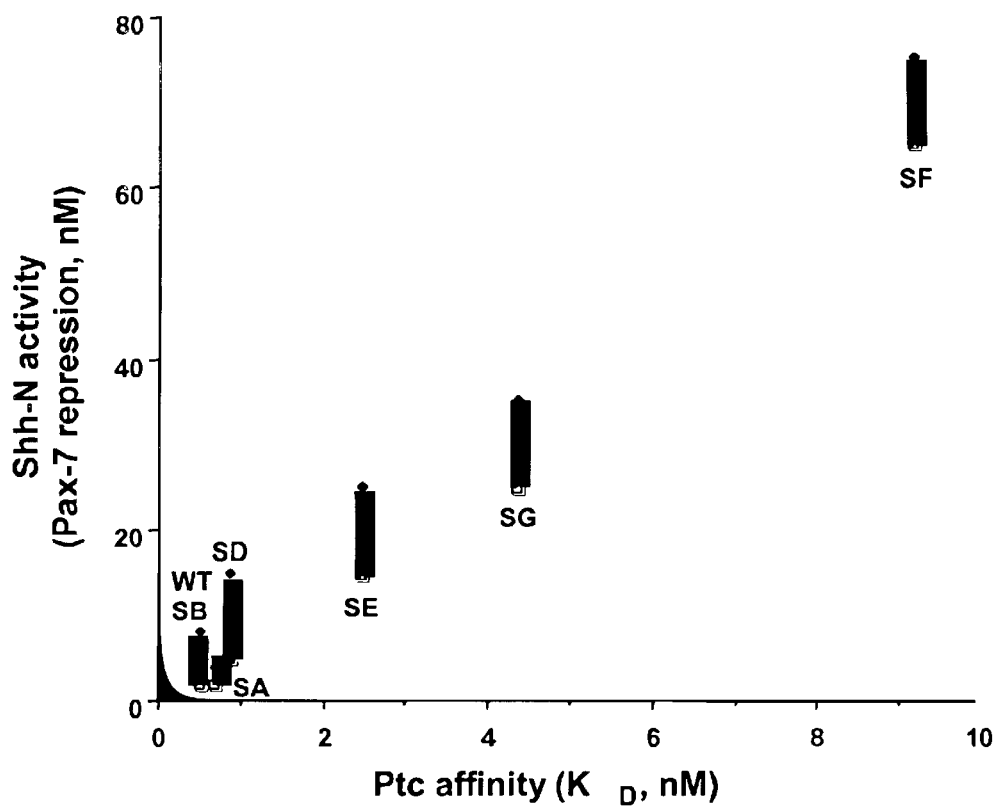

FIG. 3C

LOCUS SHH_MOUSE
DEFINITION SONIC HEDGEHOG PROTEIN PRECURSOR (SHH) (HHG-1).
ACCESSION Q62226

```
MLLLLARCFL VILASSLLVC PGLACGPGRG FGKRRHPKKL TPLAYKQFIP
NVAEKTLGAS GRYEGKITRN SERFKELTPN YNPDIIFKDE ENTGADRLMT
QRCKDKLNAL AISVMNQWPG VKLRVTEGWD EDGHHSEESL HYEGRAVDIT
TSDRDRSKYG MLARLAVEAG FDWVYYESKA HIHCSVKAEN SVAAKSGGCF
PGSATVHLEQ GGTKLVKDLR PGDRVLAADD QGRLLYSDFL TFLDRDEGAK
KVFYVIETLE PRERLLLTAA HLLFVAPHND SGPTPGPSAL FASRVRPGQR
VYVVAERGGD RRLLPAAVHS VTLREEEAGA YAPLTAHGTI LINRVLASCY
AVIEEHSWAH RAFAPFRLAH ALLAALAPAR TDGGGGGSIP AAQSATEARG
AEPTAGIHWY SQLLYHIGTW LLDSETMHPL GMAVKSS
```

Double underlined sequence is a GCF autoprocessing site.

FIG. 4

SEQUENCE LISTING

```
<160> NUMBER OF SEQ ID NOS: 17

<210> SEQ ID NO 1
<211> LENGTH: 437
<212> TYPE: PRT
<213> ORGANISM: Mus musculus

<400> SEQUENCE: 1

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
    130                 135                 140
```

```
Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
        420                 425                 430

Ala Val Lys Ser Ser
        435

<210> SEQ ID NO 2
<211> LENGTH: 437
<212> TYPE: PRT
<213> ORGANISM: Artificial sequence
<220> FEATURE:
<223> OTHER INFORMATION: Altered sonic hedgehog protein

<400> SEQ

```
Gly Lys Ile Thr Arg Asn Ser Glu Arg Phe Lys Leu Thr Pro Asn
65                  70                  75                  80

Tyr Asn Pro Asp Ile Ile Phe Lys Asp Glu Asn Thr Gly Ala Asp
            85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Lys Leu Arg Val Thr Glu Gly
        115                 120                 125

Trp Asp Glu Asp Gly His Ala Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
            290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 3
<211> LENGTH: 437
<212> TYPE: PRT
<213> ORGANISM: Artificial sequence
<220> FEATURE:
<223> OTHER INFORMATION: Altered sonic hedgehog protein
```

<400> SEQUENCE: 3

```
Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
            35                  40                  45

Ile Pro Asn Val Ala Glu Lys Thr Leu Gly Ala Ser Gly Arg Tyr Glu
50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
            115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Ala Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
            290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
```

```
                  405                 410                 415
Ile Gly Thr Trp Leu Leu Asp Ser Glu Thr Met His Pro Leu Gly Met
            420                 425                 430

Ala Val Lys Ser Ser
        435
```

<210> SEQ ID NO 4
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 4

```
Met Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
                20                  25                  30

Lys Arg His Pro Lys Lys Leu Thr Pro Leu Ala Tyr Lys Gln Phe
            35                  40                  45

Ile Pro Asn Val Ala Glu Lys Thr Leu Gly Ala Ser Gly Arg Tyr Glu
        50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His Ala Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Ala Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
```

```
                 325                 330                 335
His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 5
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 5

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Ala Ala Leu Thr Pro Asn
65                  70                  75                  80

Ala Asn Pro Asp Ile Ile Phe Lys Asp Glu Glu Asn Thr Gly Ala Asp
                85                  90                  95

Arg Leu Met Thr Gln Arg Cys Lys Ala Lys Leu Asn Ala Leu Ala Ile
            100                 105                 110

Ser Val Met Ala Gln Trp Pro Gly Val Lys Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Ala Asn Ser Val
            180                 185                 190

Ala Ala Ala Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
```

-continued

```
                    245                 250                 255
Glu Thr Leu Glu Pro Arg Glu Arg Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 6
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 6

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Ala Ala Ala Glu Lys Ala Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Ala Ala Gly Phe Asp Trp Val Tyr Tyr
```

```
                        165                 170                 175
Glu Ser Lys Ala His Ile His Cys Ser Val Lys Ala Glu Asn Ser Val
                180                 185                 190
Ala Ala Lys Ser Gly Gly Cys Phe Pro Gly Ser Ala Thr Val His Leu
            195                 200                 205
Glu Gln Gly Gly Thr Lys Leu Val Lys Asp Leu Arg Pro Gly Asp Arg
        210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Leu Glu Pro Arg Glu Arg Leu Leu Leu Thr Ala Ala His Leu
            260                 265                 270
Leu Phe Val Ala Pro His Asn Asp Ser Gly Pro Thr Pro Gly Pro Ser
        275                 280                 285
Ala Leu Phe Ala Ser Arg Val Arg Pro Gly Gln Arg Val Tyr Val Val
    290                 295                 300
Ala Glu Arg Gly Gly Asp Arg Arg Leu Leu Pro Ala Ala Val His Ser
305                 310                 315                 320
Val Thr Leu Arg Glu Glu Glu Ala Gly Ala Tyr Ala Pro Leu Thr Ala
                325                 330                 335
His Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
        355                 360                 365
Ala His Ala Leu Leu Ala Ala Leu Ala Pro Ala Arg Thr Asp Gly Gly
    370                 375                 380
Gly Gly Gly Ser Ile Pro Ala Ala Gln Ser Ala Thr Glu Ala Arg Gly
385                 390                 395                 400
Ala Glu Pro Thr Ala Gly Ile His Trp Tyr Ser Gln Leu Leu Tyr His
                405                 410                 415
Ile Gly Thr Trp Leu Leu Asp Ser Glu Thr Met His Pro Leu Gly Met
            420                 425                 430
Ala Val Lys Ser Ser
        435

<210> SEQ ID NO 7
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 7

Met Leu Leu Leu Leu Ala Arg Cys Phe Leu Val Ile Leu Ala Ser Ser
1               5                   10                  15
Leu Leu Val Cys Pro Gly Leu Ala Cys Gly Pro Gly Arg Gly Phe Gly
                20                  25                  30
Lys Arg Arg His Pro Lys Lys Leu Thr Ala Leu Ala Tyr Ala Gln Phe
            35                  40                  45
Ile Pro Asn Val Ala Glu Lys Thr Leu Gly Ala Ser Gly Arg Tyr Glu
        50                  55                  60
Gly Lys Ile Thr Arg Asn Ser Glu Arg Phe Lys Glu Leu Thr Pro Asn
65                  70                  75                  80
Tyr Asn Pro Asp Ile Ile Phe Lys Asp Glu Glu Asn Thr Gly Ala Asp
```

```
                85                  90                  95
Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
            115                 120                 125

Trp Asp Glu Asp Gly His His Ser Glu Glu Ser Leu His Tyr Glu Gly
        130                 135                 140

Arg Ala Val Asp Ile Thr Thr Ser Asp Ala Asp Arg Ala Lys Tyr Gly
145                 150                 155                 160

Met Leu Ala Arg Leu Ala Val Glu Ala Gly Phe Asp Trp Val Tyr Tyr
                165                 170                 175

Glu Ala Ala His Ile His Cys Ser Val Lys Ala Glu Asn Ser Val
            180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
            210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Thr Ala Ala His Leu
            260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
            290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 8
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 8

Met Leu Leu Leu Leu Ala Arg Cys Phe Leu Val Ile Leu Ala Ser Ser
```

-continued

```
  1               5               10              15
Leu Leu Val Cys Pro Gly Leu Ala Cys Gly Pro Gly Arg Gly Phe Gly
             20              25              30

Lys Arg Arg His Pro Lys Lys Leu Thr Pro Leu Ala Tyr Lys Gln Phe
             35              40              45

Ile Pro Asn Val Ala Glu Lys Thr Leu Gly Ala Ser Gly Arg Tyr Glu
 50              55              60

Gly Lys Ile Thr Arg Asn Ser Glu Arg Phe Lys Glu Leu Thr Pro Asn
 65              70              75              80

Tyr Asn Pro Asp Ile Ile Phe Lys Asp Ala Glu Asn Thr Gly Ala Asp
                 85              90              95

Arg Leu Met Thr Gln Arg Cys Lys Asp Lys Leu Asn Ala Leu Ala Ile
             100             105             110

Ser Val Met Asn Gln Trp Pro Gly Val Lys Leu Arg Val Thr Glu Gly
             115             120             125

Trp Asp Glu Ala Gly His His Ser Glu Ala Ser Leu His Tyr Glu Gly
             130             135             140

Arg Ala Val Asp Ile Thr Thr Ser Asp Arg Asp Arg Ser Lys Tyr Gly
145             150             155             160

Met Leu Ala Arg Leu Ala Val Glu Ala Gly Phe Asp Trp Val Tyr Tyr
                 165             170             175

Glu Ser Lys Ala His Ile His Cys Ser Val Lys Ala Glu Asn Ser Val
                 180             185             190

Ala Ala Lys Ser Gly Gly Cys Phe Pro Gly Ser Ala Thr Val His Leu
             195             200             205

Glu Gln Gly Gly Thr Lys Leu Val Lys Asp Leu Arg Pro Gly Asp Arg
             210             215             220

Val Leu Ala Ala Asp Asp Gln Gly Arg Leu Leu Tyr Ser Asp Phe Leu
225             230             235             240

Thr Phe Leu Asp Arg Asp Glu Gly Ala Lys Lys Val Phe Tyr Val Ile
                 245             250             255

Glu Thr Leu Glu Pro Arg Glu Arg Leu Leu Leu Thr Ala Ala His Leu
             260             265             270

Leu Phe Val Ala Pro His Asn Asp Ser Gly Pro Thr Pro Gly Pro Ser
             275             280             285

Ala Leu Phe Ala Ser Arg Val Arg Pro Gly Gln Arg Val Tyr Val Val
             290             295             300

Ala Glu Arg Gly Gly Asp Arg Arg Leu Leu Pro Ala Ala Val His Ser
305             310             315             320

Val Thr Leu Arg Glu Glu Glu Ala Gly Ala Tyr Ala Pro Leu Thr Ala
                 325             330             335

His Gly Thr Ile Leu Ile Asn Arg Val Leu Ala Ser Cys Tyr Ala Val
                 340             345             350

Ile Glu Glu His Ser Trp Ala His Arg Ala Phe Ala Pro Phe Arg Leu
                 355             360             365

Ala His Ala Leu Leu Ala Ala Leu Ala Pro Ala Arg Thr Asp Gly Gly
             370             375             380

Gly Gly Gly Ser Ile Pro Ala Ala Gln Ser Ala Thr Glu Ala Arg Gly
385             390             395             400

Ala Glu Pro Thr Ala Gly Ile His Trp Tyr Ser Gln Leu Leu Tyr His
                 405             410             415

Ile Gly Thr Trp Leu Leu Asp Ser Glu Thr Met His Pro Leu Gly Met
             420             425             430
```

```
Ala Val Lys Ser Ser
        435

<210> SEQ ID NO 9
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 9

Met Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Ala Leu Ala Tyr Ala Gln Phe
                35                  40                  45

Ile Pro Asn Val Ala Glu Lys Thr Leu Gly Ala Ser Gly Arg Tyr Glu
        50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Lys Leu Arg Val Thr Glu Gly
            115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
        210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350
```

-continued

```
Ile Glu Glu His Ser Trp Ala His Arg Ala Phe Ala Pro Phe Arg Leu
            355                 360                 365
Ala His Ala Leu Leu Ala Ala Leu Ala Pro Ala Arg Thr Asp Gly Gly
        370                 375                 380
Gly Gly Gly Ser Ile Pro Ala Ala Gln Ser Ala Thr Glu Ala Arg Gly
385                 390                 395                 400
Ala Glu Pro Thr Ala Gly Ile His Trp Tyr Ser Gln Leu Leu Tyr His
                405                 410                 415
Ile Gly Thr Trp Leu Leu Asp Ser Glu Thr Met His Pro Leu Gly Met
            420                 425                 430
Ala Val Lys Ser Ser
        435

<210> SEQ ID NO 10
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 10

Met Leu Leu Leu Leu Ala Arg Cys Phe Leu Val Ile Leu Ala Ser Ser
1               5                  10                  15
Leu Leu Val Cys Pro Gly Leu Ala Cys Gly Pro Gly Arg Gly Phe Gly
            20                  25                  30
Lys Arg Arg His Pro Lys Lys Leu Thr Pro Leu Ala Tyr Lys Gln Phe
        35                  40                  45
Ile Pro Asn Val Ala Glu Lys Thr Leu Gly Ala Ser Gly Arg Tyr Glu
    50                  55                  60
Gly Lys Ile Thr Arg Asn Ser Glu Arg Phe Lys Glu Leu Thr Pro Asn
65                  70                  75                  80
Tyr Asn Pro Asp Ile Ile Phe Lys Asp Glu Glu Asn Thr Gly Ala Asp
                85                  90                  95
Arg Leu Met Thr Gln Arg Cys Lys Asp Lys Leu Asn Ala Leu Ala Ile
            100                 105                 110
Ser Val Met Asn Gln Trp Pro Gly Val Lys Leu Arg Val Thr Glu Gly
        115                 120                 125
Trp Asp Glu Asp Gly His His Ser Glu Glu Ser Leu His Tyr Glu Gly
    130                 135                 140
Arg Ala Val Asp Ile Thr Thr Ser Asp Ala Asp Arg Ala Lys Tyr Gly
145                 150                 155                 160
Met Leu Ala Arg Leu Ala Val Glu Ala Gly Phe Asp Trp Val Tyr Tyr
                165                 170                 175
Glu Ser Lys Ala His Ile His Cys Ser Val Lys Ala Glu Asn Ser Val
            180                 185                 190
Ala Ala Lys Ser Gly Gly Cys Phe Pro Gly Ser Ala Thr Val His Leu
        195                 200                 205
Glu Gln Gly Gly Thr Lys Leu Val Lys Asp Leu Arg Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Leu Glu Pro Arg Glu Arg Leu Leu Leu Thr Ala Ala His Leu
            260                 265                 270
```

```
Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 11
<211> LENGTH: 437
<212> TYPE: PRT
<213> ORGANISM: Artificial sequence
<220> FEATURE:
<223> OTHER INFORMATION: Altered sonic hedgehog protein

<400> SEQUENCE: 11

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ala Ala Ala His Ile His Cys Ser Val Lys Ala Glu Asn Ser Val
            180                 185                 190
```

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
            245                 250                 255

Glu Thr Leu Glu Pro Arg Glu Arg Leu Leu Thr Ala Ala His Leu
    260                 265                 270

Leu Phe Val Ala Pro His Asn Asp Ser Gly Pro Thr Pro Gly Pro Ser
    275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
            325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
            405                 410                 415

Ile Gly Thr Trp Leu Leu Asp Ser Glu Thr Met His Pro Leu Gly Met
            420                 425                 430

Ala Val Lys Ser Ser
        435

<210> SEQ ID NO 12
<211> LENGTH: 165
<212> TYPE: PRT
<213> ORGANISM: Artificial sequence
<220> FEATURE:
<223> OTHER INFORMATION: Altered sonic hedgehog protein

<400> SEQUENCE: 12

Arg Arg His Pro Lys Lys Leu Thr Pro Leu Ala Tyr Lys Gln Phe Ile
1               5                   10                  15

Pro Asn Val Ala Glu Lys Thr Leu Gly Ala Ser Gly Arg Tyr Glu Gly
            20                  25                  30

Lys Ile Thr Arg Asn Ser Glu Arg Phe Lys Glu Leu Thr Pro Asn Tyr
        35                  40                  45

Asn Pro Asp Ile Ile Phe Lys Asp Glu Glu Asn Thr Gly Ala Asp Arg
    50                  55                  60

Leu Met Thr Gln Arg Cys Lys Asp Lys Leu Asn Ala Leu Ala Ile Ser
65                  70                  75                  80

Val Met Asn Gln Trp Pro Gly Val Lys Leu Arg Val Thr Glu Gly Trp
            85                  90                  95

Asp Glu Asp Gly His His Ser Glu Glu Ser Leu His Tyr Glu Gly Arg
            100                 105                 110

```
Ala Val Asp Ile Thr Thr Ser Asp Arg Asp Arg Ser Lys Tyr Gly Met
            115                 120                 125

Leu Ala Arg Leu Ala Val Glu Ala Gly Phe Asp Trp Val Tyr Tyr Glu
        130                 135                 140

Ala Ala Ala His Ile His Cys Ser Val Lys Ala Glu Asn Ser Val Ala
145                 150                 155                 160

Ala Lys Ser Gly Gly
                165

<210> SEQ ID NO 13
<211> LENGTH: 154
<212> TYPE: PRT
<213> ORGANISM: Artificial sequence
<220> FEATURE:
<223> OTHER INFORMATION: Altered sonic hedgehog protein

<400> SEQUENCE: 13

Tyr Lys Gln Phe Ile Pro Asn Val Ala Glu Lys Thr Leu Gly Ala Ser
1               5                   10                  15

Gly Arg Tyr Glu Gly Lys Ile Thr Arg Asn Ser Glu Arg Phe Lys Glu
            20                  25                  30

Leu Thr Pro Asn Tyr Asn Pro Asp Ile Ile Phe Lys Asp Glu Glu Asn
        35                  40                  45

Thr Gly Ala Asp Arg Leu Met Thr Gln Arg Cys Lys Asp Lys Leu Asn
    50                  55                  60

Ala Leu Ala Ile Ser Val Met Asn Gln Trp Pro Gly Val Lys Leu Arg
65                  70                  75                  80

Val Thr Glu Gly Trp Asp Glu Asp Gly His His Ser Glu Glu Ser Leu
                85                  90                  95

His Tyr Glu Gly Arg Ala Val Asp Ile Thr Thr Ser Asp Arg Asp Arg
            100                 105                 110

Ser Lys Tyr Gly Met Leu Ala Arg Leu Ala Val Glu Ala Gly Phe Asp
        115                 120                 125

Trp Val Tyr Tyr Glu Ser Lys Ala His Ile His Cys Ser Val Lys Ala
    130                 135                 140

Glu Asn Ser Val Ala Ala Lys Ser Gly Gly
145                 150

<210> SEQ ID NO 14
<211> LENGTH: 149
<212> TYPE: PRT
<213> ORGANISM: Artificial sequence
<220> FEATURE:
<223> OTHER INFORMATION: Altered sonic hedgehog protein

<400> SEQUENCE: 14

Pro Asn Val Ala Glu Lys Thr Leu Gly Ala Ser Gly Arg Tyr Glu Gly
1               5                   10                  15

Lys Ile Thr Arg Asn Ser Glu Arg Phe Lys Glu Leu Thr Pro Asn Tyr
            20                  25                  30

Asn Pro Asp Ile Ile Phe Lys Asp Glu Glu Asn Thr Gly Ala Asp Arg
        35                  40                  45

Leu Met Thr Gln Arg Cys Lys Asp Lys Leu Asn Ala Leu Ala Ile Ser
    50                  55                  60

Val Met Asn Gln Trp Pro Gly Val Lys Leu Arg Val Thr Glu Gly Trp
65                  70                  75                  80

Asp Glu Asp Gly His His Ser Glu Glu Ser Leu His Tyr Glu Gly Arg
```

```
                         85                  90                  95
Ala Val Asp Ile Thr Thr Ser Asp Arg Asp Arg Ser Lys Tyr Gly Met
                100                 105                 110

Leu Ala Arg Leu Ala Val Glu Ala Gly Phe Asp Trp Val Tyr Tyr Glu
            115                 120                 125

Ser Lys Ala His Ile His Cys Ser Val Lys Ala Glu Asn Ser Val Ala
        130                 135                 140

Ala Lys Ser Gly Gly
145

<210> SEQ ID NO 15
<211> LENGTH: 140
<212> TYPE: PRT
<213> ORGANISM: Artificial sequence
<220> FEATURE:
<223> OTHER INFORMATION: Altered sonic hedgehog protein

<400> SEQUENCE: 15

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Thr Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
                100                 105                 110

Glu Glu Ser Leu His Tyr Glu Gly Arg Ala Val Asp Ile Thr Thr Ser
            115                 120                 125

Asp Arg Asp Arg Ser Lys Tyr Gly Met Leu Ala Arg
        130                 135                 140

<210> SEQ ID NO 16
<211> LENGTH: 78
<212> TYPE: PRT
<213> ORGANISM: Artificial sequence
<220> FEATURE:
<223> OTHER INFORMATION: Altered sonic hedgehog protein

<400> SEQUENCE: 16

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Thr Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Cys
65                  70                  75

<210> SEQ ID NO 17
<211> LENGTH: 90
```

-continued

```
<212> TYPE: PRT
<213> ORGANISM: Streptomyces albus

<400> SEQUENCE: 17

Ala Leu Val Thr Met Trp Lys Leu Gln Ala Met Arg His Ala Met Gly
1               5                   10                  15

Asp Lys Pro Ile Thr Val Asn Gly Gly Phe Arg Ser Val Thr Cys Asn
                20                  25                  30

Ser Asn Val Gly Gly Ala Ser Asn Ser Arg His Met Tyr Gly His Ala
            35                  40                  45

Ala Asp Leu Gly Ala Gly Ser Gln Gly Phe Cys Ala Leu Ala Gln Ala
        50                  55                  60

Ala Arg Asn His Gly Phe Thr Glu Ile Leu Gly Pro Gly Tyr Pro Gly
65                  70                  75                  80

His Asn Asp His Thr His Val Ala Gly Gly
                85                  90
```

METHOD OF USE OF SONIC HEDGEHOG PROTEIN AS A LIGAND FOR PATCHED

RELATED APPLICATIONS

This application claims the benefit of priority under 35 U.S.C. § 119 of Provisional Application No. 60/235,153, filed Sep. 22, 2000, incorporated herein in its entirety.

FIELD OF INVENTION

The invention relates generally to methods for identifying compounds that modulate early events in development and more particularly to methods to identify compounds that modulate differentiation of neural plate using hedgehog proteins as ligands for the patched receptor.

BACKGROUND OF THE INVENTION

The diverse functions of the nervous system, which range from sensory perception and motor coordination to motivation and memory, depend on precise connections formed between distinct types of nerve cells. The development of this complex system occurs in several steps. In vertebrates, first, a uniform population of neural progenitor cells called neural plate cells are recruited from the sheet of ectodermal cells that have not yet committed to a specific pathway of differentiation. Once recruited, neural plate cells rapidly begin to differentiate, acquiring new properties that characterize the cells as immature neurons and glial cells. The first signaling event that allows a single cell type, that is neural plate cells, to give rise to a large number of neuronal and cell types depends on multiple biochemical factors and processes (see, for example, Principles in Neural Science (4th), eds. Kandel, Schwartz and Jessell, Elsevier Science Publishing Company: N.Y., 2000).

The differentiation of the neural plate from uncommitted ectoderm depends on signals secreted by a group of cells called the organizer region. Cells from the organizer region produce factors that induce and suppress development of neural tissues. Mesodermal cells in the organizer region and in the notochord provide an inductive signal that is mediated by a protein called sonic hedgehog. Sonic hedgehog is a member of a family of proteins related to the gene hedgehog (hh). This single protein, acting through short range and long range signaling activities can induce the differentiation of several mature neuronal types: floor plate cells, motor neurons and ventral interneurons.

The hedgehog gene was first identified and isolated in *Drosophila* where its multiple roles include patterning of larval segments and adult appendages. Vertebrate hh homologues also are involved in many aspects of developmental patterning. Hedgehog protein biogenesis has been best studied for the *Drosophila* protein but very likely is similar for Hedgehog proteins from all species. After cleavage of an amino-terminal signal sequence on entry into the secretory pathway, the Hh protein undergoes an intramolecular autoprocessing reaction that involves internal cleavage between the Gly-Cys residues of an absolutely conserved Gly-Cys-Phe (GCF) tripeptide. The amino-terminal product of this cleavage, which is the species active in signaling, also receives a covalent cholesteryl adduct. Autoprocessing at this site and covalent linkage to cholesterol have been experimentally confirmed for the Shh protein.

In *Drosophila*, a hedgehog protein from a construct truncated at the internal site of cleavage is active in signaling, but this protein is not spatially restricted in its signaling activity and therefore causes gross mispatterning and lethality in embryos. The autoprocessing reaction thus is required not only to release the active signal from the precursor but also to specify the appropriate spatial distribution of this signal within developing tissues, presumably through insertion of the cholesteryl moiety into the lipid bilayer of the plasma membrane. Recent studies also have revealed palmitoylation of the amino-terminal cysteine of the amino-terminal signaling domain of the Shh secreted protein (Shh-N); the occurrence of this second lipid modification is regulated by autoprocessing and may also influence the activity and distribution of Shh-N.

Several components have been identified as candidates for receptor function in transduction of the hh protein signal. The patched (ptc) gene, originally identified in *Drosophila*, encodes a multipass transmembrane protein, a patched receptor (Ptc). ptc mutations in *Drosophila* embryos cause inappropriate activation of wingless gene expression, a phenotype opposite that of hh mutations, thus suggesting that ptc functions as a negative effector in hh signaling. The observations that hh ptc double mutant embryos resemble ptc mutants and that, in a ptc mutant background, ectopic Hh expression produces no further phenotypic effects, together suggest that the Ptc gene product acts downstream of Hh to regulate its signaling activity. Genetic epistasis studies further suggest that the smoothened gene (smo), which encodes another transmembrane protein (Smo), functions downstream of ptc in the hh signaling cascade. Because smo is required for hh signaling, it has been proposed that Smo activates the Hh pathway and that Ptc inhibits Smo activity. Genetic mosaic analysis in the *Drosophila* wing imaginal disc showed that Ptc has, in addition to a cell-autonomous negative effect on Hh signaling, an ability to sequester the Hh protein and prevent its movement to adjacent cells.

Vertebrate homologues of both ptc and smo genes have been identified. Shh-N was found to bind to cells expressing Ptc or both Ptc and Smo, but not to cells expressing Smo alone. Moreover, Ptc interacted with Smo independently of the presence of Shh-N, suggesting that the two transmembrane proteins form a complex. An integrated view of *Drosophila* genetic analyses and biochemical studies of vertebrate homologues suggests a model in which the Ptc-Smo complex might function as Hh receptor, with direct binding of Hh to Ptc releasing Smo activity from inhibition by Ptc. It must be noted, however, that these biochemical studies did not examine the role of a physical interaction between Shh-N and Ptc in activation of the Shh pathway. In addition, these biochemical studies did not exclude the possibility that Shh-N interacts not directly with Ptc but with another component of a complex that includes Ptc, because the crosslinked binding complexes were extremely large and were not analyzed with regard to their composition.

The model just described assumes a role for Shh-N as a ligand for a receptor. The crystal structure of the Shh-N protein, however, suggested an alternative possibility. This structure revealed a zinc ion coordinated in an arrangement remarkably similar to that of thermolysin, carboxypeptidase A, and other zinc hydrolases. Even more striking is the remarkable similarity in folded structure of a portion of Shh-N to the catalytic domain of D,D-carboxypeptidase from *Streptomyces albus*, a cell wall enzyme closely related in structure and activity to other bacterial enzymes involved in conferring vancomycin resistance. Although the functional role of this putative hydrolase in Shh-N is not known, one possibility is that signaling requires Shh-N hydrolytic activity on as yet unknown substrates. Thus, several fundamental questions about the mechanisms of Shh-N signaling remain unanswered. To illuminate these issues, the present invention provides Shh-N mutations that abolish zinc hydrolase activity within Shh-N and Shh-N proteins with alterations in evolutionarily conserved surface residues.

BRIEF DESCRIPTION OF INVENTION

In one embodiment of the invention, there is provided an isolated protein having the amino acid sequence of sonic hedgehog amino terminal protein, wherein alanine is substituted for the amino acid residue at one or more positions selected from position 51, 52, 56, 75, 90, 76, 81, 105, 116, 132, 135, 138, 168, 177, 189 and 195, and combinations of the positions.

In another embodiment of the invention, there is provided an isolated protein including the amino acid sequence set forth in a sequence selected from SEQ ID NO:1, SEQ ID NO:2, SEQ ID NO:3 SEQ ID NO:4; SEQ ID NO:5, SEQ ID NO:6, SEQ ID NO:8 and SEQ ID NO:12.

In yet another embodiment of the invention, there is provided a method for identifying a compound that modulates a cellular response mediated by a hedgehog protein. The method includes incubating the compound with a cell expressing a hedgehog protein and a patched receptor under conditions sufficient to permit the compound with the patched receptor or the hedgehog protein. A cellular response mediated by a hedgehog protein in the cell incubated with the compound is compared with the response of a cell not incubated with the compound. A difference in response between the cell incubated with the compound and the cell not incubated with the compound is indicative of a compound that modulates a cellular response mediated by the hedgehog protein.

In another embodiment of the invention, there is provided a method for identifying a compound that modulates a cellular response mediated by a patched receptor. The method includes incubating the compound with a cell expressing the patched receptor and a hedgehog protein under conditions sufficient to permit the compound to interact with the cell. The cellular response in a cell incubated with the compound is compared with the cellular response of a cell not incubated with the compound. A difference in response is indicative of a compound that modulates a cellular response mediated by the patched receptor.

In yet another embodiment of the invention, there is provided a method for identifying a compound that modulates differentiation of neural plate cells. The method includes incubating the compound and a hedgehog protein with neural plate cells expressing a patched receptor under conditions sufficient to permit the compound to interact with the cell. The differentiation of neural plate cells incubated with the compound is compared with the differentiation of neural plate cells not incubated with the compound. A difference in differentiation of neural plate cells incubated with the compound compared to differentiation of neural plate cells incubated without the compound is indicative of a compound that modulates differentiation of neural plate cells.

In still another embodiment of the invention, there is provided a method for increasing the stability of a hedgehog protein. The method includes introducing a thiol-containing amino acid into the amino acid of a hedgehog protein. The residue may be introduced at residues 51, 52, 56, 75, 90, 76, 81, 105, 116, 132, 135, 138, 168, 177, 189, 195, or combinations thereof.

In yet another embodiment of the invention, there is provided a method of modifying the pharmacokinetic properties of a hedgehog protein. The method includes introducing into the amino acid sequence of a hedgehog protein a thiol-containing amino acid and modifying the introduced amino acid by attaching a maleimide-linked moiety.

In yet a further embodiment of the invention, there is provided a method of identifying a surface amino acid of a hedgehog protein involved in hedgehog signaling. The method includes incubating a hedgehog protein having one or more substituted amino acid residues and cell expressing a patched receptor under conditions that allow the hedgehog protein to interact with the cell. Hedgehog-mediated signaling is then assayed.

BRIEF DESCRIPTION OF THE FIGURES

FIG. 1 shows a likely catalytic site in Shh-N.

FIG. 2 shows direct binding of Shh-N to Ptc. FIGS. 2A and 2B show Scatchard analysis of the high-affinity component of $^{32}$P-Shh-N binding to EcR-293 cells expressing Ptc (C) or Ptc-CTD (D).

FIG. 2C shows a summary of predicted molecular masses of Ptc and Ptc-CTD, experimental values estimated from Western blotting, and apparent masses of crosslinked products. Experimental values are the average of several independent determinations. Also shown are estimates of the binding coefficients of Shh-N for Ptc and for Ptc-CTD, and estimates of the number of binding sites per cell.

FIG. 3 shows binding of altered Shh-N proteins to Ptc.

FIG. 3C shows signaling activity as a function of Ptc affinity. On the basis of neural plate signaling assays, protein concentrations required for Pax-7 repression are plotted as a function of Ptc-binding affinity. The protein concentrations are plotted as ranges centered about the concentrations presented in Table 1. Note that there is an excellent correlation between Ptc binding and activity in Pax-7 repression. The zinc hydrolase mutants EA (SEQ ID NO:3), HA (SEQ ID NO:2), and EH (SEQ ID NO:4) (Table 1) also corroborate this correlation but are omitted for clarity.

FIG. 4 shows the amino acid sequence of sonic hedgehog protein (SEQ ID NO:1). Autoproteolytic site is double underlined.

DETAILED DESCRIPTION OF THE INVENTION

Figure 1A:
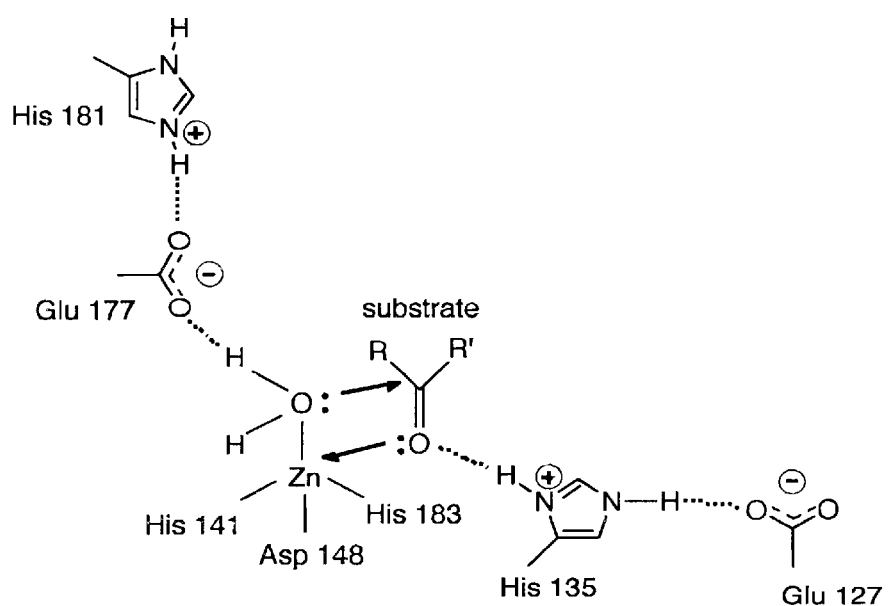
FIG. 1A shows a model for an apparent zinc hydrolase catalytic site derived from the crystal structure of Shh-N. Glu-177 and His-135 residues are presumed to be essential for catalysis, and His-141, Asp-148, and His-183 coordinate the $Zn^{2+}$ ion.
Figure 1B:
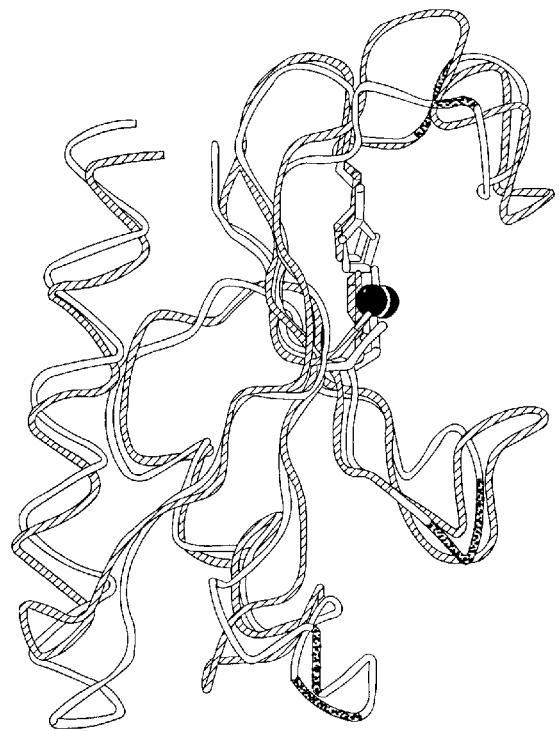
FIG. 1B shows superimposed alpha-carbon traces of Shh-N and D,D-carboxypeptidase from *Streptomyces albus*. The portion of these proteins displaying structural homology is drawn, with the $Zn^{2+}$ ions shown as shaded spheres. Residues within the structurally homologous portion of Shh-N that are altered in SC (four of six) and SD (two of three) are located in structurally diverged loops.

The present invention relates to methods for identifying compounds that modulate developmental processes mediated by hedgehog proteins. Hedgehog proteins, a family of secreted signaling molecules, are involved in pattern formation during embryogenesis. Sonic hedgehog protein, synthesized in the notochord, can induce neural plate cells to differentiate into ventral cell types such as floor plate cells and motor neurons. Differentiation is induced by a hedgehog protein signal that acts through a transmembrane receptor. The interaction of the hedgehog protein and the transmembrane receptor is therefore a key element in modulation of differentiation during development.

The invention provides hedgehog proteins that act as signals in development. As used herein, hedgehog (hh) proteins constitutes a family of secreted signaling molecules that govern patterns of cellular differentiation during embryogenesis (reviewed in Perrimon, N. (1995) *Cell* 80, 517–520; Hammerschmidt et al. (1997) *Trends Genet.* 13, 14–21; and Goodrich and Scott (1998) *Neuron* 21, 1243–1257). The hedgehog (hh) gene was first identified and isolated in *Drosophila*, where its multiple roles include patterning of larval segments and adult appendages. Vertebrate hh homologues also are involved in many aspects of developmental patterning. The Sonic hedgehog (Shh) member of this family, for example, is required for patterning of the neural tube and other tissues (Chiang et al. (1996) *Nature (London)* 383, 407–413).

Hedgehog protein biogenesis (reviewed in Beachy et al. (1997) *Cold Spring Harbor Symp. Quant. Biol.* 62, 191–204) has been best studied for the *Drosophila* protein but very likely is similar for Hedgehog proteins from all species. After cleavage of an amino-terminal signal sequence on entry into the secretory pathway, the Hh protein undergoes an intramolecular autoprocessing reaction that involves internal cleavage between the Gly-Cys residues of an absolutely conserved GCF tripeptide (Lee et al, (1994) *Science* 266, 1528–1537; and Porter, et al. (1995) *Nature (London)* 374, 363–366). The amino-terminal product of this cleavage, which is the species active in signaling, also receives a covalent cholesteryl adduct (Porter et al. (1996) *Science* 274, 255–259). Autoprocessing at this site and covalent linkage to cholesterol have been experimentally confirmed for the Shh protein. In *Drosophila*, a hedgehog protein from a construct truncated at the internal site of cleavage is active in signaling, but this protein is not spatially restricted in its signaling activity and therefore causes gross mispatterning and lethality in embryos (Porter et al (1996) *Cell* 86, 21–34). The autoprocessing reaction thus is required not only to release the active signal from the precursor but also to specify the appropriate spatial distribution of this signal within developing tissues, presumably through insertion of the cholesteryl moiety into the lipid bilayer of the plasma membrane. Recent studies also have revealed palmitoylation of the amino-terminal cysteine of the amino-terminal signaling domain of the Shh secreted protein (Shh-N); the occurrence of this second lipid modification is regulated by autoprocessing and may also influence the activity and distribution of Shh-N (Pepinsky et al. (1998) *J. Biol. Chem.* 237, 14037–14045).

The signaling domain of the hedgehog protein is the amino terminal domain. As used herein, "amino terminal domain" is an amino acid sequence derived from amino terminal amino acids of a hedgehog protein and having at its carboxy terminus, a glycine-cysteine-phenylalanine (Gly-Cys-Phe) cleavage site specifically recognized by a proteolytic activity of the carboxy terminal fragment of the native hedgehog polypeptide. This fragment is denoted the amino (NH2)-terminal domain or polypeptide, herein. For example, in the case of mouse sonic hedgehog, the NH2 domain includes amino acids 34 to 198 of sonic hedgehog protein (SEQ ID NO:12). The Gly-Cys-Phe cleavage site in mouse hedgehog precursor protein occurs at amino acid residues 198–200 of the full sequence (see FIG. 4, SEQ ID NO:1). In the case of the *Drosophila* hedgehog, the amino domain includes amino acids 1–257 of hedgehog protein. The Gly-Cys-Phe cleavage site in *Drosophila* hedgehog precursor protein occurs at amino acid residues 257–259 of the full sequence *Drosophila* hedgehog protein. Those of skill in the art will be able to identify the Gly-Cys-Phe cleavage site in other hedgehog proteins, as the amino acid location will be similar and the site will be specifically recognized by the autoproteolytic activity of the corresponding carboxy (COCH) terminal fragment.

The amino-terminal protein is also characterized by being cell-associated in cells expressing the protein in vitro, and being specifically localized in vertebrate or *Drosophila* cells or embryos. In other words, this amino-terminal fragment of hedgehog, remains close to the site of cellular synthesis. The association of the amino terminal domain with the cell is a result of the processing event that involves lipophilic modification of the amino terminal domain. This modification is initiated by the action of the carboxy terminal domain, generating a thioester intermediate; the carboxy-terminal domain thus does not act simply as a protease, although cleavage of a peptide bond does ultimately result from its action. Specifically, the lipid modification is a cholesterol moiety. In addition, the amino terminal fragment binds to heparin agarose in vitro. The hedgehog protein from which the amino terminal domain is derived includes proteins derived from *Drosophila, Xenopus*, chicken, zebrafish, mouse, and human.

One exemplary hedgehog amino terminal domain protein is set forth in SEQ ID NO:1. Sonic hedgehog amino domain protein (Shh-N), formed by amino acid residues 25–198 of precursor sonic hedgehog, is a fragment of a wild type sonic hedgehog protein. As used herein, "wild type" refers to protein sequences as they are found in nature, without manipulation, alteration or modification of the sequence of amino acids. Hedgehog amino terminal proteins are provided in U.S. Pat. No. 6,281,332 Aug. 28, 2001, herein incorporated by reference, in its entirety.

Moreover, it will be generally appreciated that, under certain circumstances, it may be advantageous to provide altered sonic hedgehog protein which function as a hedgehog antagonist, in order to inhibit all or only a subset of the biological activities of the naturally-occurring form of the protein. Thus, specific biological effects can be elicited by treatment with an altered protein, and with fewer side effects relative to treatment with agonists or antagonists which are directed to all of the biological activities of naturally occurring forms of hedgehog proteins.

Proteins contemplated by the present invention include altered sonic hedgehog amino terminal proteins having one or more amino acid substitutions in the sequence of the protein. Altered sonic hedgehog terminal domain proteins have some or all functional properties of wild type sonic hedgehog terminal domain proteins. Such functional properties may be elicited by exposure to altered proteins at concentrations in the range of the concentration of wild type protein, or by concentrations one to ten, to twenty, to thirty orders of magnitude greater than the concentration of wild type protein.

An amino acid substitution refers to the substitution of one amino acid residue for another in the sequence of the protein. In one embodiment of the invention, the amino acid alanine is substituted for the amino acid residue at one or more positions selected from positions 51, 52, 56, 75, 76, 81, 90, 105, 116, 132, 135, 138, 177, 189 and 195.

Exemplary proteins include a sonic hedgehog amino terminal protein having alanine substituted for histidine at position 135 (SEQ ID NO:2), a sonic hedgehog protein having alanine substituted for glutamic acid at position 177 (SEQ ID NO:3), a sonic hedgehog amino terminal protein having alanine substituted for histidine at position 135 and alanine substituted for glutamic acid at position 177 (SEQ ID NO:4), a sonic hedgehog amino terminal protein having alanine substituted for lysine at position 75, alanine for glutamic acid at position 76, alanine for tyrosine at position 81, alanine for aspartic acid at position 105, alanine for asparagine at position 116, alanine for glutamic acid at position 189, and alanine for lysine at position 195 (SEQ ID NO:5), a sonic hedgehog amino terminal protein having alanine for asparagine at position 51, alanine for valine at position 52, alanine for threonine at position 56, and alanine for glutamic acid at position 168 (SEQ ID NO:6), and a sonic hedgehog amino terminal protein having alanine for glutamic acid at position 90, alanine for aspartic acid at position 132, and alanine for glutamic acid at position 138 (SEQ ID NO:8).

Exemplary proteins further include sonic hedgehog amino terminal domain protein wherein the amino acid alanine is substituted for the amino acid residue at one or more positions selected from positions 42, 46, 154, 157, 178 and 179. Exemplary proteins include a sonic hedgehog amino terminal protein having alanine substituted for proline at position 42, alanine substituted for lysine at position 46, alanine substituted for arginine at position 154, alanine substituted for serine at position 157, alanine substituted for serine at position 178 and alanine substitute for lysine at position 179 (SEQ ID NO:7); a sonic hedgehog amino terminal protein having alanine substituted for proline at position 42 and alanine substituted for lysine at position 46 (SEQ ID NO:9); a sonic hedgehog amino terminal protein having alanine substituted for arginine at position 154f and alanine substitute for serine at position 157 (SEQ ID NO:10); and a sonic hedgehog amino terminal protein having alanine substituted for serine at position 178 and alanine substituted for lysine at position 179 (SEQ ID NO:11).

In other embodiments of the invention, there are provided sonic hedgehog amino terminal proteins having a deletion of one or more amino acids from the wild type sequence. For example, a protein having from one to ten amino acids deleted from the amino terminal is contemplated. In one embodiment, a sonic hedgehog amino terminal protein having nine amino acids deleted from the amino terminal of sonic hedgehog amino terminal protein, resulting in a protein comprising amino acids 34 to 198 of wild-type sonic hedgehog amino terminal protein (SEQ ID NO:12) is contemplated by the present invention. Further exemplary "deletion proteins" contemplated by the invention include a sonic hedgehog amino terminal protein having twenty amino acids deleted from the amino terminal of sonic hedgehog amino terminal protein, resulting in a protein having amino acids 45 to 198 of wild-type sonic hedgehog amino terminal protein (SEQ ID NO:13); a sonic hedgehog amino terminal protein having 25 amino acids deleted from the amino terminal of sonic hedgehog amino terminal protein, resulting in a protein having amino acids 50 to 198 of wild-type sonic hedgehog amino terminal protein (SEQ ID NO:14); a sonic hedgehog amino terminal protein having residues 166 to the carboxy terminus deleted resulting a protein having amino acids 25 to 165 of wild-type sonic hedgehog amino terminal protein (SEQ ID NO:15); and a sonic hedgehog amino terminal protein having residues 103 to the carboxy terminus deleted resulting in a protein having amino acids 25 to 101 of wild type sonic hedgehog amino terminal protein (SEQ ID NO:16).

Altered hedgehog amino terminal proteins can be generated by mutagenesis, such as by discrete point mutation(s), or by truncation. For instance, mutation can give rise to proteins which retain substantially the same, or merely a subset, of the biological activity of the hh protein from which it was derived. Alternatively, antagonistic forms of the protein can be generated which are able to inhibit the function of the naturally occurring form of the protein, such as by competitively binding to an hh receptor.

In general, protein referred to herein as having an activity of a hh protein are defined as polypeptides which mimic or antagonize all or a portion of the biological/biochemical activities of a naturally occurring hedgehog protein. Examples of such biological activity include the ability to induce (or otherwise modulate) differentiation of neural plate cells, the ability to modulate the formation and differentiation of the head, limbs, lungs, central nervous system (CNS), digestive tract or other gut components, or mesodermal patterning of developing vertebrate and invertebrate embryos. Hedgehog proteins, especially Shh, can constitute a general ventralizing activity. For instance, the subject protein can be characterized by an ability to induce and/or maintain differentiation of neurons, e.g., motorneurons, cholinergic neurons, dopaminergic neurons, serotonergic neurons, peptidergic neurons and the like. In certain embodiments, the biological activity can comprise an ability to regulate neurogenesis, such as a motor neuron inducing activity, a floor plate inducing activity, a neuronal differentiation inducing activity, or a neuronal survival promoting activity. Hedgehog proteins of the present invention can also have biological activities which include an ability to regulate organogensis, such as through the ability to influence limb patterning, by, for example, skeletogenic activity. The biological activity associated with the hedgehog proteins of the present invention can also include the ability to induce stem cell or germ cell differentiation, including the ability to induce differentiation of chondrocytes or an involvement in spermatogenesis.

The terms "induction" or "induce", as relating to the biological activity of a hedgehog protein, refers generally to the process or act of causing to occur a specific effect on the phenotype of cell. Such effect can be in the form of causing a change in the phenotype, e.g., differentiation to another cell phenotype, or can be in the form of maintaining the cell in a particular cell, e.g., preventing dedifferentiation or promoting survival of a cell.

The term isolated as used herein also refers to a protein or peptide that is substantially free of cellular material, viral material, or culture medium when produced by recombinant DNA techniques, or chemical precursors or other chemicals when chemically synthesized. The term "substantially pure" as used herein refers to hedgehog amino terminal proteins that are substantially free of other proteins, lipids, carbohydrates, nucleic acids or other materials with which it is naturally associated. One skilled in the art can purify hedgehog proteins using standard techniques for protein purification. The substantially pure protein will yield a single major band on a non-reducing polyacrylamide gel. The purity of the hedgehog protein can also be determined by amino-terminal amino acid sequence analysis.

The invention includes a functional amino terminal hedgehog protein, and functional fragments thereof. As used herein, the term "functional protein" or "functional fragment" refers to a protein that possesses a biological function or activity identified through a defined functional assay and that is associated with a particular biologic, morphologic, or phenotypic alteration in the cell.

Minor modifications of the amino terminal protein amino acid sequence may result in protein which have substantially equivalent activity as compared to the amino terminal protein described herein. Such modifications may be deliberate, as by site-directed mutagenesis, or may be spontaneous.

The amino terminal protein of the invention also includes conservative variations of the polypeptide sequence. The term "conservative variation" as used herein denotes the replacement of an amino acid residue by another biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Also provided by the invention is a method of modifying the pharmacokinetic properties of a hedgehog protein. The method includes introducing into the amino acid sequence of a hedgehog protein a thiol-containing amino acid at position 51, 52, 56, 75, 90, 76, 81, 105, 116, 132, 135, 138, 168, 177, 189, 195, or combinations thereof, and modifying the introduced amino acid by attaching a maleimide-linked moiety. Hedgehog amino terminal proteins can be modified to alter its pharmacokinetic properties. For example, cysteine residues can be introduced at locations away from or distal to the region involved in binding to the patched receptor. Regions not required for binding can be predicted from the altered proteins described herein and by methods known in the art (see, for example, Pepinsdy et al. (2000) J. Biol. Chem. 275:10995–1101, incorporated by reference herein). Such cysteine residues can be specifically targeted by using maleimide-linked moieties, for example to attach polyethylene glycol (PEG) moieties to various positions in the protein without altering properties required for binding to Ptc or for signaling. Modifications to hedgehog proteins alter their pharmacokinetic properties including rendering a hedgehog protein more stable, increasing its ability to bind to proteins, increasing its ability to resist binding to inhibitors or otherwise resist the effects of inhibitory signals, and the like.

Modification of the subject proteins could be effected to alter binding properties of the proteins. For example, HIP-1 is a sonic hedgehog amino terminal protein binding protein. It can interact with sonic hedgehog amino terminal protein and inhibit the activity of sonic hedgehog amino terminal protein. Modification of the altered proteins can be achieved so that sonic hedgehog amino terminal proteins are able to bind to patched receptor and function as a signaling molecule, but they could not bind to HIP-1. This modification can result in a protein that is more active in the presence of HIP-1, e.g., in vivo (see Chuang and McMahon (1999) Nature 18:397:617–21).

The invention includes antibodies immunoreactive with or which bind to hedgehog amino terminal proteins or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and F(ab').sub.2, which are capable of binding an epitopic determinant on hedgehog proteins. The antibodies of the invention include antibodies which bind to the hedgehog amino terminal proteins and which bind with immunoreactive fragments such proteins.

The term "antibody" as used in this invention includes intact molecules as well as fragments thereof, such as Fab, F(ab').sub.2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; $F(ab')_2$ is a dimer of two Fab' fragments held together by two disulfide bonds; (4) Fv, defined as a genetically engineered fragment containing the variable genetically fused single chain molecule. Methods of making these fragments are known in the art. (See for example, Harlow and Lane, Antibodies: A Laboratory Manual, Cold Spring Harbor laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. It is recognized in the art that antibodies that can distinguish between altered or mutated proteins can be prepared. For example, an antibody that can specifically identify a hedgehog protein having an alanine substitution at position 135 (SEQ ID NO:2) can be prepared.

Antibodies that bind to the hedgehog amino terminal protein of the invention can be prepared using an intact polypeptide or fragments containing small peptides of interest as the immunizing antigen. The protein used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991). It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first monoclonal antibody.

Monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays that are run in either the forward, reverse, or simultaneous modes, including immunohistochemical assays on physiological samples. Those of skill in the art will know, or can readily discern, other immunoassay formats without undue experimentation.

Monoclonal antibodies can be bound-to many different carriers and used to detect the presence of a hedgehog amino terminal protein. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

Hedgehog amino terminal proteins may be detected by the monoclonal antibodies when present in biological fluids and tissues. Any sample containing a detectable amount of a hedgehog amino terminal protein can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or anti-heterophilic immunoglobulins to anti hedgehog amino terminal protein present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

In another embodiment of the invention there is provided a method for identifying a compound that modulates a cellular response mediated by a hedgehog protein. The method includes incubating the compound with a cell expressing a hedgehog protein and a patched receptor under conditions sufficient to permit the compound to interact with the patched receptor, and comparing a cellular response mediated by a hedgehog protein in the cell incubated with the compound with the response of a cell not incubated with the compound. A difference in response between the cell incubated with the compound and the cell not incubated with the compound is indicative of a compound that modulates a cellular response mediated by the hedgehog protein A "cellular response" as used herein, is an event or sequence of events that singly or together are a direct or indirect response by a cell to a hedgehog protein. Such a cellular response can be modulation of one or more of growth, differentiation, or survival of a cell responsive to hedgehog induction.

A cellular response includes response by neural plate cells. Neural plate cells differentiate into various specific cell types. Both floor plate cells and motor neurons are induced to form from neural plate cells. Accordingly, the cellular response can be an increase or decrease in induction of differentiation of floor plate cells, and an increase or decrease in induction of differentiation of motor neurons.

A cellular response further includes an increase or decrease in repression of a dorsal neural tube cell marker. Concentration-dependent actions of sonic hedgehog in the developing neural tube include suppression of dorsal markers (Pax-3, Gli-3, Ephrin A5), activation of ventral marker genes (HNF3beta, patched, N$\alpha$2.2, netrin-1), and induction of ventral neurons (dopaminergic, serotonergic) and ventrolateral motor neurons (Islet-1+, Islet-2+, HB9+) and interneurons (Engrailed-1+, CHX10+) (Hynes et al. (2000) Nat. Neurosci. 3:41–46).

In the vertebrate embryo, the somites arise from the paraxial mesoderm as paired mesodermal units in a craniocaudal sequence. Segmentation is also the underlying principle of the body plan in annelids and arthropods. Genes controlling segmentation have been identified that are highly conserved in organisms belonging to different phyla. Segmentation facilitates movement and regionalization of the vertebrate body; in humans, for example, one can see the results of such regionalization in vertebral bodies, intervertebral disks, ribs, and spinal nerves. Somite research shows that each somite consists of an outer epithelium and a mesenchymal core. Later, the ventral portion of the somite undergoes de-epithelialization and gives rise to the sclerotome, whereas the dorsal portion forms the dermomyotome. The dermomyotome is the source of myotomal muscle cells and the dermis of the back. It also yields the hypaxial muscle buds at flank level and the myogenic cells invading the limb buds. The dorsal and ventral somitic domains express different sets of developmental control genes, for example, those of the Pax family (Brand-Saberi and Christ (2000) Curr. Top. Dev. Biol. 48:1–42) including Pax-1, Pax-3 and Pax-7.

The method can be carried out with hedgehog proteins that mimics the effects of a naturally-occurring hedgehog protein on the cell, as well as with proteins that antagonize the effects of a naturally-occurring hedgehog protein on said cell. Hedgehog proteins contemplated in the practice of the invention include wild-type hedgehog amino terminal protein, and altered hedgehog amino terminal proteins as described herein.

The method includes incubating the compound with a cell expressing a patched receptor (Ptc). The tumor suppressor gene patched (ptc) encodes an approximately 140 kDa polytopic transmembrane protein that binds members of the Hedgehog (Hh) family of signaling proteins and regulates the activity of Smoothened (Smo), a G protein-coupled receptor-like protein essential for hedgehog signal transduction. Ptc contains a sterol-sensing domain (SSD), a motif found in proteins implicated in the intracellular trafficking of cholesterol and/or other cargoes. Cholesterol plays a critical role in hedgehog signaling by facilitating the regulated secretion and sequestration of the hedgehog protein, to which it is covalently coupled. In addition, cholesterol synthesis inhibitors block the ability of cells to respond to hedgehog, and this finding points to an additional requirement for the lipid in regulating downstream components of the hedgehog signaling pathway. Although the SSD of Ptc has been linked to both the sequestration of, and the cellular response to hedgehog, definitive evidence for its function has so far been lacking. It is likely that Ptc controls Smo activity by regulating an intracellular trafficking process dependent upon the integrity of the SDD.

Compounds that modulate a cellular response can include peptides, peptidomimetics, polypeptides, pharmaceuticals, chemical compounds and biological agents. Antibodies and combinatorial compound libraries can also be tested using the method of the invention. One class of chemical compounds includes organic molecules, preferably small organic compounds having a molecular weight of more than 50 and less than about 2,500 Daltons. Candidate compounds comprise functional groups necessary for structural interaction with proteins, for example with a hedgehog amino terminal protein or with a patched receptor, particularly hydrogen bonding, and typically include at least an amine, carbonyl, hydroxyl or carboxyl group, preferably at least two of the functional chemical groups. The candidate compound often comprises cyclical carbon or heterocyclic structures and/or aromatic or polyaromatic structures substituted with one or more of the above functional groups.

The compound may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., *Science* 242:229–237, 1988) and cloning have been reviewed (Sambrook et al., *Molecular Cloning: a Laboratory Manual*, 2nd Ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate compounds are also found among biomolecules including, but not limited to: peptides, saccharides, fatty acids, steroids, purines, pyrimidines, derivatives, structural analogs or combinations thereof.

A variety of other agents in addition to those specifically named may be included in the screening assay. These include agents such as salts, neutral proteins, e.g., albumin, detergents, etc. that are used to facilitate optimal protein-protein binding and/or reduce nonspecific or background interactions. Reagents that improve the efficiency of the assay, such as protease inhibitors, nuclease inhibitors, antimicrobial agents and the like may be used. The components are added to the incubation mixture in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

Also provided by the invention is a method for identifying a compound that modulates a cellular response mediated by a patched receptor. The method includes incubating the compound with a cell expressing the patched receptor and a hedgehog protein under conditions sufficient to permit the compound to interact with the cell and comparing a cellular response in a cell incubated with the compound with the cellular response of a cell not incubated with the compound. A difference in response is indicative of a compound that modulates a cellular response mediated by the patched receptor.

Also provided by the invention is a method for identifying a compound that modulates differentiation of neural plate cells. The method includes incubating the compound and a hedgehog protein with neural plate cells incubates with the compound with the differentiation of neural plate cells not incubated with the compound. A difference in differentiation of neural plate cells incubated with the compound compared to differentiation of neural plate cells incubated without the compound is indicative of a compound that modulates differentiation of neural plate cells.

Also provided by the invention is a method of identifying a surface amino acid of a hedgehog protein involved in hedgehog signaling. The method includes incubating a hedgehog protein having one or more substituted amino acid residues and a cell expressing a patched receptor under conditions that allow the hedgehog protein to interact with the cell; and assaying hedgehog-mediated signaling by the cell. A difference in hedgehog mediated signaling in the cell incubated with the hedgehog protein as compared to hedgehog mediated signaling in a cell not incubated with the hedgehog protein is indicative of a hedgehog protein involved in hedgehog signaling. A surface amino acid of a hedgehog protein is an amino acid that, is on an outer surface of the tertiary or three-dimensional structure of the protein. Such surface amino acids, or their side chains are exposed to interactions with other molecules.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Preparation of Recombinant Shh-N Mutant Proteins. Constructs for altered Shh-N were made by standard methods (Ausubel et al.(1994) *Current Protocols in Molecular Biol-* ogy (Wiley, N.Y.)). Recombinant proteins were expressed in *Escherichia coli* and purified as described in Roelink et al. ((1995) *Cell* 81, 445–455). To prepare the $^{32}$P-labeled Shh-N protein, a protein kinase A site tag (RRASV) was introduced at the carboxy terminus of Shh-N, and the tagged Shh-N was phosphorylated in a reaction containing [γ-$^{32}$P]ATP. Cy2-labeled recombinant Shh-N was prepared by using CyDye FluoroLink Reactive Dye (Amersham).

Chicken Neural Plate Explant Culture Chicken intermediate neural plate explant culture methods have been described in Roelink et al. (1995, supra) and Cooper et al. ((1998) *Science* 280, 1603–1607). Neural plate explants were stained with either mouse anti-Pax-7 [PAX7, Developmental Studies Hybridoma Bank (DSHB)], rabbit anti-hepatocyte nuclear factor (HNF)-3β (K2, a gift from T. M. Jessell, Columbia University), or mouse anti-Islet-1(40.2D6, DSHB) antibodies.

Cell Culture for Ptc Expression Fragments encoding full-length mouse Ptc and carboxyl-terminal Myc-tagged Ptc-CTD (Ptc with a truncation resulting in a 140-residue carboxyl-terminal deletion; amino acids nos. 1-1,291, a gift from M. P. Scott, Stanford University) were inserted into pIND(Sp) vector (Invitrogen). To make stable cell lines, EcR-293 cells (Invitrogen) were transfected with recombinant constructs or empty vector, and several independent clones for each construct were isolated.

Shh-N-Ptc-Binding Assay. Ptc expression was induced in cloned stable derivatives of the cell line EcR-293 by addition of ponasterone A (Invitrogen). After induction, 2.5×10$^5$ cells were mixed with increasing concentrations (0.1 nM-50 nM) of $^{32}$P-Shh-N (for Scatchard analyses) or with a fixed concentration (0.9 nM) of $^{32}$P-Shh-N and various concentrations of competitors (for competitive binding assays). After incubation at 4° C., cells were collected, and the bound $^{32}$P-Shh-N was determined. For the qualitative Ptc-binding assay, QT6 cells transiently transfected with pRK5-Ptc-CTD were incubated with 2 nM Cy2-labeled Shh-N protein and 160 nM unlabeled competitor. The ability of the unlabeled protein to compete for binding of Cy2-Shh-N protein to cells was directly observed by fluorescence microscopy.

Crosslinking of $^{32}$P-Shh-N to Ptc. Induced EcR-293 cells were incubated with the $^{32}$P-labeled Shh-N at a final concentration of 2 nM at 4° C. Unlabeled Shh-N was added as competitor to 200 nM. After the cells were washed once with PBS, labeled Shh-N was crosslinked to cells by adding freshly prepared disuccinimidyl suberate (Pierce) to 5 mM in PBS and incubating for 50 min. at 4° C. Crosslinked cells were washed with cold PBS and lysed in 0.15 mM NaCl/0.05 mM Tris.HCl, pH 7.2/1% Triton X-100/1% sodium deoxycholate/0.1% SDS (RIPA) buffer containing proteinase inhibitors. Lysate proteins were fractionated by SDS/PAGE (6%) and visualized by staining with Coomassie blue. After the gel was dried, crosslinked products were visualized by autoradiography.

EXAMPLE 2

Zinc Hydrolase Activity is not Required for Shh-N Signaling

Figures 1C, 1D:
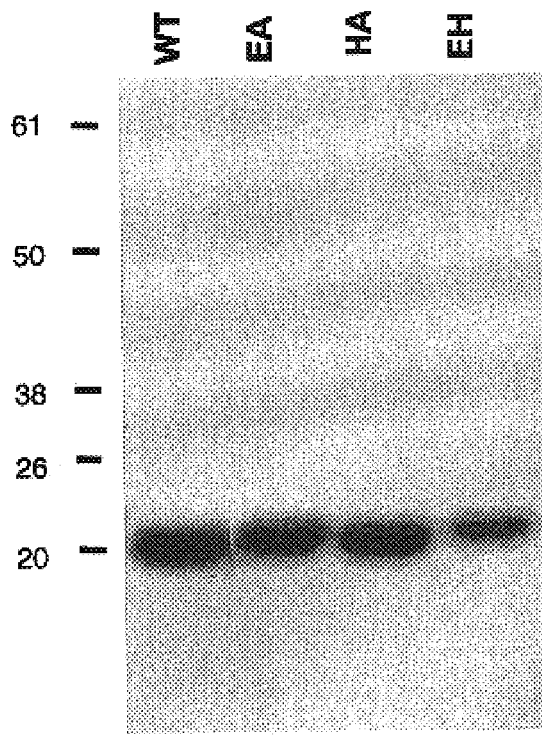
FIG. 1C shows Coomassie blue staining of purified recombinant wild type (WT) and E177A (EA), H135A (HA) and double mutant (EH) Shh-N proteins resolved in SDS/PAGE (15%); molecular mass markers are indicated at left (kDa).
FIG. 1D shows structure-based alignment of amino acid sequence from the portions of mouse Shh (mSHH) (residues 100–187 of SEQ ID NO:1) and *Streptomyces albus* D,D-carboxypeptidase (DD-C) (SEQ ID NO:17) shown in FIG. 1B. The residues involved in zinc coordination or hydrogen bonding of the water molecule are shown in dark shading, and other conserved residues are in light shading. Target sites for mutagenesis are indicated for zinc hydrolase mutants and for SC and SD mutants.

To determine whether Shh-N acts as an enzyme, glutamate-177 (E177) and histidine-135 (H135) were substituted by alanine. E177 forms a hydrogen bond to a zinc-bound water molecule, and H135 is positioned to stabilize a potential tetrahedral intermediate (FIG. 1A; Hall et al. (1995) *Nature (London)* 378, 212–216). By analogy with other zinc hydrolases, both residues are likely to be essential for catalytic activity (Christianson, D. W. (1991) *Adv. Protein Chem.* 42, 281–355). Furthermore, the VanX protein, a structural homologue of Shh-N, displays a reduction in activity of more than six orders of magnitude on alteration of the R71 residue (Lessard and Walsh (1999) *Chem. Biol.* 6, 177–187), which corresponds to H1135 in Shh-N (Bussiere et al., (1998) *Mol. Cell* 2, 75–84). These substitutions (E177A, H135A) were introduced individually and in combination into an *E. coli* expression vector, and purified altered proteins were prepared (FIG. 1C).

A chicken intermediate neural plate explant culture system was used to test the signaling activity of recombinant proteins (Roelink et al. (1995) supra). Wild-type Shh-N protein applied to these explants induced motor neurons at 5 nM and predominantly floor plate cells at 25 nM, as monitored by expression of Islet-1 and HNF-3β, respectively. Shh-N protein at 4 nM sufficed for suppression of the dorsal marker Pax-7. The concentrations of Shh-N required for these inductive events, although slightly higher than previously reported (Roelink et al. (1995) supra; Ericson et al. (1997) *Cell* 90, 169–180; and Cooper et al.(1998) supra), were reproducible in the assay protocol used in this study.

Signaling activities of Shh-N zinc hydrolase mutants were studied in chicken intermediate neural plate explants double stained for expression of the motor neuron marker Islet-1 and the floor plate marker HNF-3β. No Islet-1- or HNF-3β positive cells were observed in control explants, whereas 5 nM and 25 nM concentrations of wild-type Shh-N induced expression of Islet-1 and HNF-3β. Explants cultured with medium only express Pax-7 but not HNF-3β. Wild-type Shh-N protein fully repressed expression of Pax-7 at 4 nM and uniformly induced HNF-3β in all cells at 20 nM. The EH (SEQ ID NO:4) and EA (SEQ ID NO:3) mutant proteins repressed Pax-7 at 4, albeit somewhat less efficiently, and were able to uniformly induce HNF-3β expression at 20. The H135A (HA) (SEQ ID NO:2) mutant protein was indistinguishable from wild type at 4 nM and at 20 nM.

All three of the zinc hydrolase mutant Shh-N proteins tested, E177A (EA) (SEQ NO:3), H135A (HA) (SEQ ID NO:2), and the double mutant (EH) (SEQ ID NO:4), retained the capacity to repress Pax-7 expression and to induce floor plate cells in the explants. Whereas the EA (SEQ ID NO:3) and EH (SEQ ID NO:4) mutant proteins displayed slightly reduced signaling activity, the HA protein (SEQ ID NO:2) was indistinguishable from wild type (SEQ ID NO:1) (Table 1). Because the altered residues are absolutely critical for catalytic activity in other zinc hydrolases (Christian (1991) supra; and Lessard and Walsh (1999) supra), retention of signaling activity by Shh-N hydrolase mutant proteins indicates that catalytic activity is not required for signaling. The reduced potency for EH (SEQ ID NO:4) and EA (SEQ ID NO:3) in signaling may reflect a destabilization of folded protein structure, as might be expected from subsitution of Ala for the largely buried side chains of the Glu-177 and His-135 residues. Indeed, the EA (SEQ ID NO:3) and EH (SEQ ID NO:4) altered proteins displayed a somewhat reduced affinity for Ptc-CTD protein, which may account for their reduced potency, whereas HA (SEQ ID NO:2) was essentially indistinguishable from wild type (Table 1; see below).

TABLE 1

| Protein | Mutation sites | Pax-7 repression, nM | HNF-3β induction, nM | Ptc-CTD affinity, nM | 5E1 IP | Heparin Binding |
|---|---|---|---|---|---|---|
| WT | Wild type (aa 25–198) | ~4 | <20 | 0.48 | ++ | + |
| HA | H135A | ~4 | ≥20 | 0.63 | ND | + |
| EA | E177A | ~10 | ≥20 | 1.7 | ND | + |
| EH | H135A, E177A | ~10 | ≥20 | 1.7 | ND | + |
| SA | K75A, E76A, Y81A, D105A, N116A, E189A, K195A | ~4 | ≤20 | 0.66 | ++ | + |
| SB | N51A, V52A, T56A, E168A | ~4 | ≥20 | 0.48 | ++ | + |
| SC | P42A, K46A, R154A, S157A, S178A, K179A | >>1,000 | >>1,000 | >>36 | – | – |
| SD | E90A, D132A, E138A | ~10 | ≥20 | 0.84 | ++ | + |
| SE | P42A, K46A | ~20 | ~100 | 2.4 | + | + |
| SF | R154A, S157A | ~70 | ≥100 | 9.1 | + | + |
| SG | S178A, K179A | ~30 | ~100 | 4.3 | + | + |

Figure 3A:
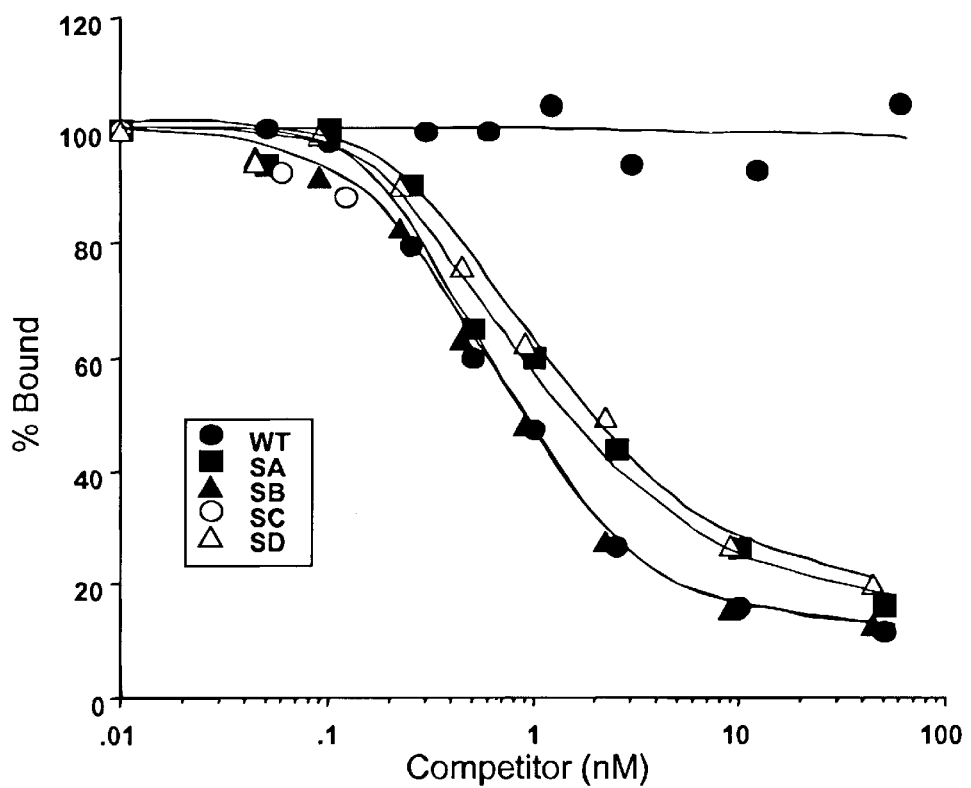
FIGS. 3A and 3B show competition by altered proteins for binding of 32P-Shh-N to EcR-293 cells expressing Ptc-CTD. Binding of 32P-Shh-N in the presence of each altered protein at various concentrations is nonnalized to the total value of 32P-Shh-N bound (approximately 35% of input) in the absence of competitor. The SC mutant (SEQ ID NO:7), inactive in signaling, also fails to compete for binding to Ptc-CTD. The SE (SEQ ID NO:9), SF (SEQ ID NO:10), and SG (SEQ ID NO:11) proteins with intermediate levels of signaling activity, displayed intermediate levels of competition for binding to Ptc-CTD. Data are summarized in Table 1.

Protein signaling was tested at initial concentrations of 4, 20, 100, 500, and 1,000 nM and subsequently at 10 nM concentration intervals for EA (SEQ ID NO:3), HA (SEQ ID NO:2), EH (SEQ ID NO:4), SD (SEQ ID NO:8), SE (SEQ ID NO:9), SF (SEQ ID NO:10), and SG (SEQ ID NO:11) (Table 1). The minimum concentration required for complete repression of Pax-7 and for uniform induction of HNF-3β is shown for each protein. As an indication of affinity for Ptc-CTD, binding coefficients (KI) for binding of mutant Shh-N proteins to Ptc-CTD were derived from competitive binding experiments in FIGS. 3A and B by using the equation $KI=[IC50]/(1+[L]/KL)$, where [IC50] is the concentration of unlabelled mutant proteins required for 50% competition. [L] is the concentration of unbound wild-type protein (32P-Shh-N) and KL is the dissociation constant for wild-type Shh-N. Immunoprecipitation by 5E1 monoclonal antibody and binding to heparin-agarose are indicated. ND, not determined.

Alterations in residues that should be critical for the putative zinc hydrolase activity of Shh-N did not disrupt its ability to induce ventral neural cell types or to suppress dorsal markers, suggesting that catalytic activity is not required for Shh signaling in the neural plate. Although residues constituting the putative zinc hydrolase active site are widely conserved among Hh family members, they are not fully conserved in *Drosophila* suggesting that hydrolase function is not required for signaling in this organism. We also introduced and ectopically expressed the E177A and EH mutant Shh constructs into *Drosophila* and compared their ability to mispattern the embryonic cuticle with that of wild-type Shh and could detect no significant difference between them (H. E. F. Takahashi and P. A. B., unpublished data), further substantiating dispensability of catalytic activity for Shh-N signaling function in the context of developing *Drosophila* embryos. Furthermore, experiments with mutant proteins expressed in cultured cells suggest that the putative hydrolase activity is not required for the normal biogenesis and processing of Shh, nor for its normal state of modification. It is also noted that no hydrolase activity of Shh-N in biochemical assays with a variety of substrates was detected, including some like those for D,D-carboxypeptidase, which contained D-amino acid residues.

The putative zinc hydrolase of Shh-N has thus resisted our attempts to reveal an activity, either in biochemical or in in vitro or in vivo signaling assays, raising the possibility that the putative catalytic site represents an evolutionary vestige of its common ancestry with the D,D-carboxypeptidase family of proteins. In this view, the zinc atom may have lost its ancestral role in catalysis but could have retained a role in stabilizing protein structure through interactions with the side chains of coordinating residues. The lack of conservation of coordinating residues in the *Drosophila* protein may indicate a replacement of these interactions by other stabilizing interactions. General dispensability of hydrolase activity in Hh signaling is consistent with the importance of surface residues conserved among Hh proteins for binding to Ptc and for signaling (see below). Alternatively, it is possible that Shh-N hydrolase retains a role not detected by our biochemical or in vitro and in vivo signaling assays. Such a role likely would be modulatory in nature, given the essentially normal signaling activity of hydrolase mutant proteins, and its discovery may require targeted recombination to mutagenize the endogenous mouse Shh gene.

EXAMPLE 3

Direct Binding of Shh-N Protein to Ptc

Because the analyses above suggested a noncatalytic function of Shh-N protein, experiments next focused on Shh-N interaction with Ptc (Stone et al. (1996) *Nature* (*London*) 384, 129–134; and Marigo et al. (1996) *Nature* (*London*) 384, 176–179). To determine whether Shh-N protein directly interacts with Ptc, stable cloned EcR-293 cell lines were generated for ecdysone-inducible expression of full length Ptc and Ptc-CTD (see Example 1). Such stable cell lines, but not a control line carrying the empty vector, expressed Ptc and Ptc-CTD proteins when induced with the ecdysone analog, ponasterone A. On protein blots probed with anti-Ptc antibody, two broad bands were detected for Ptc (dots, 168 kDa and 157 kDa) or for Ptc-CTD (dots, 163 kDa and 141 kDa). The estimated masses of the faster-migrating species were close to the molecular masses predicted from primary sequence (159 kDa for Ptc and 144 kDa for Ptc-CTD) (FIG. 2C).

For sensitive detection of Shh-N binding to Ptc, a $^{32}$P-labeled Shh-N protein was prepared by introducing a protein kinase A (PKA) site at the carboxy terminus of Shh-N followed by labeling of the purified recombinant protein with PKA and γ-$^{32}$P]ATP. Ptc and Ptc-CTD expression was examined in stably transfected cloned cell lines. Cell lysates were prepared from stable EcR-293 cell lines carrying pIND(Sp) (empty vector control), pIND(Sp)-Ptc, or pIND (Sp)-Ptc-CTD, and proteins were fractionated by SDS/PAGE (6%) followed by blotting and detection with anti-Ptc antibody (Santa Cruz Biotechnology). Two bands (dots) were detected in lysates from Ptc or from Ptc-CTD cells, but not from control cells. Crosslinking of $^{32}$P-labeled Shh-N protein to Ptc and Ptc-CTD. EcR-293 cells expressing Ptc and Ptc-CTD were incubated with $^{32}$P-Shh-N protein in absence (−) or presence (+) of a 100-fold excess of unlabeled Shh-N protein and then crosslinked. Cell lysates were subjected to SDS/PAGE (6%) and crosslinked products detected by autoradiography. Autoradiographic images for control and Ptc and for Ptc-CTD are presented at distinct contrast settings to highlight the crosslinked species. Addition of this kinase site at the carboxy terminus did not affect signaling activity of Shh-N. Crosslinking of $^{32}$P-labeled Shh-N protein to EcR-293 cells expressing Ptc or Ptc-CTD was performed in the presence of a bivalent crosslinker, disuccinimidyl suberate. Crosslinked products were detected in lysates of Ptc and Ptc-CTD cells, but not in those of control cells. These crosslinked species were abolished by competition with unlabeled Shh-N protein, demonstrating a specific interaction. The crosslinked species form a single band, not two as detected in Western blotting, suggesting that a particular form of Ptc or Ptc-CTD might bind to Shh-N. The estimated molecular masses of the crosslinked products (172 kDa for Ptc and 158 kDa for Ptc-CTD) differ by 14 kDa, which corresponds closely to the differences in mass between Ptc and Ptc-CTD and definitively indicates the participation of Ptc and Ptc-CTD in these complexes. The apparent masses of these complexes furthermore are close to the sums of the masses of Shh-N plus Ptc or of Shh-N plus Ptc-CTD (178 kDa and 163 kDa, respectively) (FIG. 2C), suggesting a 1:1 stoichiometry of Ptc and Shh-N in these complexes. These results strongly suggest that Shh-N interacts directly with Ptc protein.

Quantitative analysis of $^{32}$P-Shh-N binding to these cells revealed a high-affinity Ptc-dependent component of binding that could be competed by nanomolar concentrations of unlabeled Shh-N and a low-affinity component that was not dependent on Ptc expression and that could not be competed by Shh-N. Scatchard analysis of the Ptc- and Shh-N-specific high affinity component (FIGS. 2A and 2B) indicated that the binding coefficients of Ptc and Ptc-CTD for $^{32}$P-Shh-N protein are similar (0.58 nM and 0.48 nM respectively; FIG. 2C). Assuming, as argued above, that one Shh-N ligand binds to one Ptc molecule, the number of binding sites per cell for Ptc-CTD (210,000) is about 5.5 times higher than that for Ptc (38,000) (FIG. 2C). The temperature utilized in these binding studies (4° C.) is not permissive of endocytosis, indicating that Shh-N binding initially occurs on the cell surface, even though immunofluorescence studies clearly demonstrate that Ptc and Ptc-CTD proteins are predominantly localized inside cells. The difference in number of binding sites for these two proteins thus could be caused either by a higher degree of surface localization for Ptc-CTD or, alternatively, by a higher level of Ptc-CTD expression as compared with Ptc, a phenomenon also consistently observed in transiently transfected. Thus, at present one cannot distinguish whether the 140 residues absent from Ptc-CTD influence the subcellular localization of the Ptc protein or its steady-state levels within the cell.

EXAMPLE 4

The Role of Shh-N Surface Residues in Signaling and in Ptc Binding

Having demonstrated a direct and high-affinity interaction between Ptc and Shh-N, the significance of this interaction was determined by examining the correlation between Ptc binding and signaling potency of altered Shh-N proteins. The Shh-N protein was subjected to systematic mutagenesis to identify surface residues involved in signaling and potential ligand/receptor interactions. Because Hh proteins can act similarly across species and in distinct biological settings [Shh, for example, is active in Drosophila (Chang et al. (1994) Development (Cambridge, U.K.) 120, 3339–3353; and Krauss et al. (1993) Cell 75, 1431–1444) and distinct vertebrate proteins can act in common pathways (Ekker et al. (1995) Development (Cambridge, U.K.) 121, 2337–2347)], it seems likely that surface residues potentially important in inductive activities and ligand/receptor interactions would be conserved. The Shh-N structure was used to identify surface residues based on degree of side chain exposure to solvent (Hall et al. (1995) supra). Among these surface residues, those that are evolutionarily conserved were geographically divided into four major regions named SA, SB, SC, and SD and subjected to mutagenesis. Four mutant proteins were generated, SEQ ID NOS:5, 6, 7, and 8, respectively, each containing multiple alanine substitutions at the conserved surface residues within each region (see Table 1). Because the side chains of the residues selected are solvent exposed, it was expected that the folded structures of these proteins would not be affected.

The altered proteins were purified and applied to chicken neural plate explant cultures. The SA (SEQ ID NO:5) and SB (SEQ ID NO:6) altered proteins repressed Pax-7 expression and induced floor plate cells in the explants as well as the wild-type protein, and the SD altered protein (SEQ ID NO:8) displayed an approximate 2.5-fold reduction in activity. In striking contrast, no signaling activity of the SC mutant (SEQ ID NO:7) could be detected even at 1 μM, a concentration 250-fold higher than that required for Pax-7 repression by wild-type protein (SEQ ID NO:1) (results summarized in Table 1). Ptc binding for these altered proteins was next examined using a competition binding assay. The SA (SEQ ID NO:5), SB (SEQ ID NO:6), and SD (SEQ ID NO:8) mutant proteins competed with the 32P-labeled wild-type Shh-N protein for binding to Ptc-CTD expressing cells as well or nearly as well as the wild-type protein (FIG. 3A), yielding similar binding coefficients (Table 1). Ptc-binding activity of the SC mutant (SEQ ID NO:7), however, was not detectable (FIG. 3A; Table 1), suggesting a possible correlation between Ptc binding and signaling activity for the Shh-N protein.

Figure 3B:
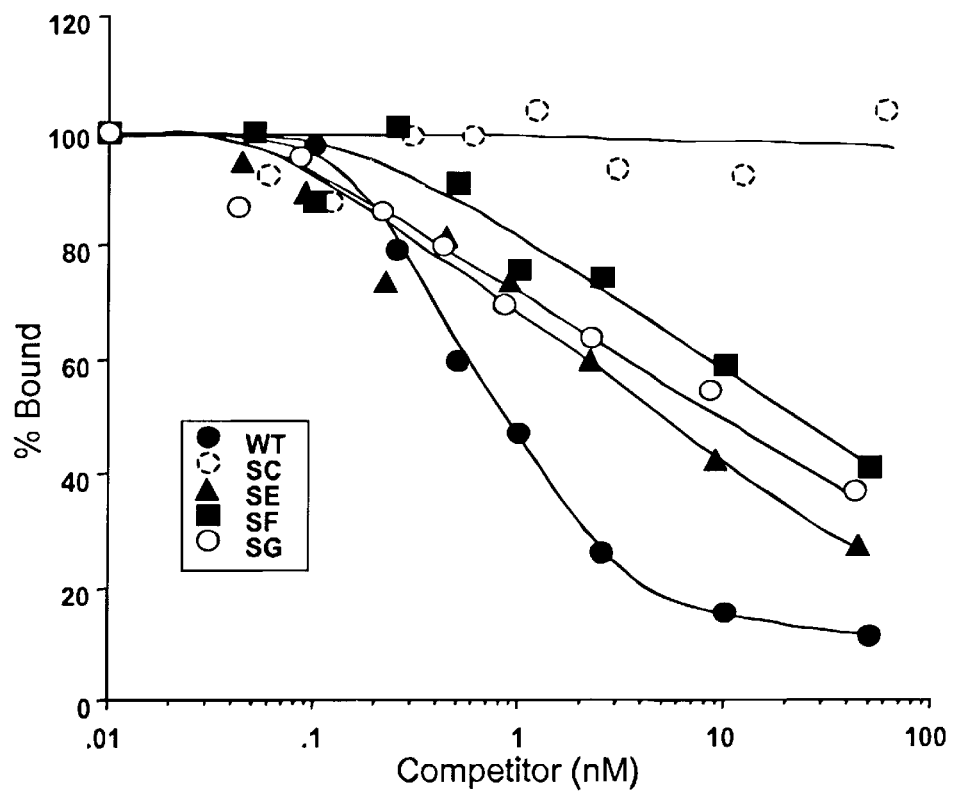

To explore this correlation further, three additional proteins (SE (SEQ ID NO:9), SF (SEQ ID NO:10), and SG (SEQ ID NO:11)) were tested, each with alterations in two amino acid residues that comprise distinct subsets of the six residues altered in SC (SEQ ID NO:7) (see Table 1). All three of these mutant proteins displayed signaling activity in the explant culture assay, but only at significantly reduced levels. At 4 nM none of these three proteins repressed Pax-7; at 20 nM the SE (SEQ ID NO:9) and SC (SEQ ID NO:11) proteins repressed Pax-7 almost completely or partially, respectively, but SF (SEQ ID NO:10) did not. At 100 mM, the SE (SEQ ID NO:9) and SG (SEQ ID NO:11) proteins induced HNF-3β expression in most cells of the explant, but SF (SEQ ID NO:10) did so only in a small number of cells. Further assays at concentration intervals of 10 nM pinpointed the minimal concentrations required for Pax-7 repression, with values of about 20, about 30, and about 70 mM for SE (SEQ ID NO;9), SG (SEQ ID NO:11), and SF (SEQ ID NO:10), respectively (results in Table 1). Competition binding assays also revealed a significantly reduced affinity of the SE (SEQ ID NO:9) and SG (SEQ ID NO:11)

proteins for Ptc-CTD, and an even lower affinity for the SF protein (SEQ ID NO:10) (FIG. 3B; Table 1). These results indicate that normal Ptc binding and neural plate signaling activities require distinct contributions from multiple individual residues in the SC (SEQ ID NO:7) surface region. Furthermore, among proteins with alterations in distinct subsets of the SC (SEQ ID NO:7) mutant residues, Ptc-binding affinity correlated extremely well with neural plate signaling activity (FIG. 3CC).

Shh-N proteins with deletions of amino- or carboxyl-terminal residues were also purified and their activities qualitatively in signaling and in Ptc binding were examined (Table 2). An altered protein lacking nine amino-terminal residues (ΔN34, SEQ ID NO:12) displayed signaling and Ptc-binding activities indistinguishable from wild type. In contrast, ΔN50 (SEQ ID NO:14, which lacks 25 amino-terminal residues, completely lost both activities. It was noted that the residues deleted in ΔN50 include P42 and K46, which were altered in the SC (SEQ ID NO:7) and SE (SEQ ID NO:9) mutant proteins, and that the mutant ΔN45 (SEQ ID NO:13) (lacking 20 amino-terminal residues), which does not contain P42, also lost signaling activity. The activity defects in these proteins are more severe than those of the SE protein (SEQ ID NO:9), suggesting that loss of these amino-terminal residues may have some effect on the overall structure or stability of the Shh-N protein. A deletion mutant lacking residues from 166 to the carboxy terminus, ΔC165 (SEQ ID NO:15), had neither signaling nor Ptc-binding activities, and ΔC101 (SEQ ID NO:16) also lost signaling activity (Table 2). These deletions also remove residues that are altered in the SC protein (SEQ ID NO:7) (R154, S157, S178, and K179 in ΔC101; S178 and K179 in ΔC165), but again, the deleted regions are sufficiently extensive that they would be expected to affect protein structure.

TABLE 2

| Protein | Residues present | HNF-3β induction | Ptc-CTD binding | 5E1 IP | Heparin binding |
|---|---|---|---|---|---|
| WT | wild type (aa 25-198) | + | + | + | + |
| ΔN34 | aa 34-198 | + | + | + | + |
| ΔN45 | aa 45-198 | – | ND | ND | – |
| ΔN50 | aa 50-198 | – | – | – | – |
| ΔC165 | aa 25-198 | – | – | – | + |
| ΔC101 | aa 25-101 | – | ND | ND | + |

The properties of the mutant proteins (Table 2) were either indistinguishable or completely different from wild type in a qualitative neural plate assay for induction of HNF3β or in a qualitative Ptc-binding competition assay using Qt6 cells transiently transfected with Ptc-CTD and Cy2-labeled sonic hedgehog amino terminal protein. Immunoprecipitation by 5E1 monoclonal antibody and binding to heparin agarose are indicated. ND indicates not determined.

In all of the altered proteins tested not a single example of a protein that retained signaling activity while losing the ability to bind Ptc was found. As seen in FIG. 3C, there is an excellent correlation between Ptc binding and signaling activity in all altered proteins for which these properties can be measured, and these results strongly suggest that Ptc binding may be a critical requirement for signaling.

Previous genetic and biochemical studies are consistent with the idea that Ptc may function as a Hh receptor. The biochemical analyses demonstrated that Shh-N protein binds to Ptc-expressing cells, that Ptc is coimmunoprecipitated with Shh-N and vice versa, and that Ptc can be crosslinked in a complex containing Shh-N. Because the composition of the crosslinked complexes was not characterized, however, these studies could not exclude the possibility that instead of binding directly to Ptc, Shh-N may bind to another component of a complex that includes Ptc. These biochemical studies also did not examine the role of such an interaction in the activation of the Shh pathway. The latter is a particularly significant issue given the genetically demonstrated role of Ptc in sequestration of Hh protein to restrict its movement within *Drosophila* tissues.

In addressing these questions, a crosslinked product containing radiolabeled Shh-N was identified that is specifically competed by unlabeled Shh-N but not by the unlabeled mutant SC protein (SEQ ID NO:7). This crosslinked complex also contains Ptc because its formation depends on Ptc expression and because it displays an apparent molecular mass difference that corresponds closely to the differences between full-length Ptc or Ptc-CTD. Finally, for both Ptc molecules, the apparent mass of the complex is close to the sum of Shh-N plus Ptc. Thus, although direct binding ideally would be demonstrated by studies with purified components, the properties of our crosslinked complexes strongly suggest a direct association between Shh-N and Ptc with a probable stoichiometry of 1:1. Given the possible anomalies in migration of such crosslinked species, we cannot rule out the possibility that more than one Shh-N molecule is present in these complexes, nor can we distinguish between the participation of the slower- or faster-migrating Ptc forms, which probably differ in their glycosylation. Although it has been reported that Ptc interacts with Smo independently of Shh-N, the apparent masses of our crosslinked products would appear to exclude Smo, which has a predicted mass of 87 kDa. It is possible that the cells utilized in the present study do not express Smo endogenously or that high-level expression of Smo is required for formation of a complex with Ptc/Shh. Alternatively, the experimental conditions for crosslinking might disrupt Ptc-Smo interaction or fail to capture Smo protein.

Also identified herein, using altered Shh-N proteins, is the region of the Shh-N protein surface that is involved in Ptc binding. These altered proteins have been used to show that neural plate signaling activity is retained in proportion to the binding affinity for Ptc. Thus, the extensive alterations in surface residues of the SA (SEQ ID NO:5), SB (SEQ ID NO:6), and SD (SEQ ID NO:8) proteins do not affect or only mildly affect Ptc binding, and these proteins retain normal or nearly normal signaling activity. At the other extreme, the SC altered protein (SEQ ID NO:7) displays a complete loss of Ptc binding, and this is reflected in a complete loss of neural plate signaling activity. Even more telling, proteins carrying distinct subsets of the residues altered in SC result in intermediate levels of Ptc-binding activity and corresponding intermediate levels of neural plate signaling activity (FIG. 3C). Multiple individual residues within the SC surface region (SEQ ID NO:7) that contribute independently to Ptc binding thus also similarly contribute to signaling potency. Although our results cannot exclude a role for interactions with other proteins in reception of the Shh signal, they do strongly suggest that direct binding to Ptc is a critical step, and this information will serve as the basis for further elucidation of downstream events.

EXAMPLE 5

Antibody Recognition and Heparin Binding of Altered Proteins

The monoclonal antibody 5E1, directed against Shh-N, blocks signaling in neural plate explants (Ericson et al.

(1996) Cell 87, 661–673) and also blocks binding of the Shh-N protein to Ptc-expressing cells. The reactivity of the 5E1 antibody with altered Shh-N proteins was examined by immunoprecipitation. All proteins that retain signaling and Ptc-binding activities, including wild type (SEQ ID NO:1), SA (SEQ ID NO:5), SB (SEQ ID NO:6), SD (SEQ ID NO:8), and ΔN34 (SEQ ID NO:12), also retain full reactivity with 5E1 (Tables 1 and 2). In contrast, the altered proteins SC (SEQ ID NO:7), ΔN50 (SEQ ID NO:14), and ΔC165 (SEQ ID NO:15), which lost both signaling and Ptc-binding activities, were not immunoprecipitated by 5E1 (Tables 1 and 2). Altered proteins with intermediate signaling and Ptc-binding properties, such as SE (SEQ ID NO:9), SF (SEQ ID NO:10), and SG (SEQ ID NO:11), displayed intermediate reactivities with 5E1 (Table 1). Reactivity of 5E1 with Shh-N proteins thus correlates well with Ptc binding and neural plate signaling activities.

Because 5E1 works well for immunoprecipitation and for immunocytochemistiy but very poorly in Western analysis, it appears to recognize an epitope present on the native Shh-N protein but not in denatured protein. The strong correlation between 5E1 binding, Ptc binding, and neural plate signaling furthermore suggests that the 5E1 epitope coincides with determinants required for these activities. One possible explanation for the coordinate loss of signaling, 5E1 binding, and Ptc binding in the SC protein (SEQ ID NO:7) is that the folded structure of this protein might be disrupted. Circular dichroism analysis, however, indicates that the secondary structure profile of SC (SEQ ID NO:7) is similar to that of wild-type Shh-N, suggesting that any disruption in folded structure must be highly local in nature. In addition, mutations in distinct subsets of the residues altered in SC (SEQ ID NO:7) display intermediate phenotypes, suggesting multiple independent contributions of individual residues in formation of the Ptc-interacting region of the protein surface.

The Shh-N protein also binds to heparin, and the crystal structure contains a sulfate anion at a location near the SC region. In addition, recent evidence suggests that tout velu, a *Drosophila* gene whose mammalian homologues function in the polymerization of glycosamines for synthesis of heparin sulfate proteoglycans (McCormick et al. (1998) Nat. Genet. 19, 158–161; and Lind et al. (1998) J. Biol. Chem. 273, 26265–8), plays a role in the reception and transport of the Hh signal (Bellaiche et al. (1998) Nature (London) 394, 85–88). Therefore tests were conducted to determine whether the alterations in these proteins affect their ability to bind to heparin agarose. As seen in Tables 1 and 2 only three of the proteins tested, SC (SEQ ID NO:7), ΔN45 (SEQ ID NO:13), and ΔN50 (SEQ ID NO:14), lost the ability to bind heparin agarose, and these three proteins are completely inactive in Ptc binding and signaling. Some of the proteins that lose signaling and Ptc-binding activity retained the ability to bind heparin, indicating that heparin binding is not sufficient for Ptc binding and for signaling. These data, however, would be consistent with the idea that heparin binding may be necessary for Ptc binding and for signaling.

While the invention has been described in detail with reference to certain preferred embodiments thereof, it will be understood that modifications and variations are within the spirit and scope of that which is described and claimed.

What is claimed is:

1. A method for identifying a compound that modulates a cellular response mediated by a hedgehog protein comprising:
   (a) incubating the compound with a neural plate cell expressing a hedgehog protein consisting essentially of SEQ ID NO:1 having an amino terminal residue corresponding to any one of residues 26 through 35 of SEQ ID NO:1, and a patched receptor under conditions sufficient to permit the compound to interact with the patched receptor or the hedgehog protein; and
   (b) comparing differentiation of the neural plate cell into a floor plate cell in the cell incubated with the compound with differentiation of a neural plate cell into a floor plate cell of a cell not incubated with the compound,
   wherein a difference in differentiation between the cell incubated with the compound and the cell not incubated with the compound is indicative of a compound that modulates a cellular response mediated by the hedgehog protein.

2. The method of claim 1, wherein the hedgehog protein has the amino acid sequence set forth in SEQ ID NO:12.

3. The method of claim 1, wherein said compound is selected from peptides, peptidomimetics, polypeptides, pharmaceuticals, chemical compounds, biological agents, antibodies, and combinatorial compound libraries.

4. A method for identifying a compound that modulates a cellular response mediated by a patched receptor comprising:
   (a) incubating the compound with a neural plate cell expressing the patched receptor and a hedgehog protein consisting essentially of SEQ ID NO:1 having an amino terminal residue corresponding to any one of residues 26 through 35 of SEQ ID NO:1, under conditions sufficient to permit the compound to interact with the neural plate cell; and
   (b) comparing differentiation of the neural plate cell into a floor plate cell in a cell incubated with the compound with differentiation of a neural plate cell into a floor plate cell of a cell not incubated with the compound, wherein a difference in differentiation is indicative of a compound that modulates a cellular response mediated by the patched receptor.

5. The method of claim 4, wherein the hedgehog protein is Sonic hedgehog amino terminal protein.

6. The method of claim 4, wherein the hedgehog protein has the amino acid sequence set forth in SEQ ID NO:12.

7. The method of claim 4, wherein the compound is selected from peptides, peptidomimetics, polypeptides, pharmaceuticals, chemical compounds, biological agents, antibodies and neurotropic agents.

8. A method for identifying a compound that modulates differentiation of neural plate cells into floor plate cells, comprising:
   (a) incubating the compound and a hedgehog protein consisting essentially of SEQ ID NO:1 having an amino terminal residue corresponding to any one of residues 26 through 35 of SEQ ID NO:1, with a neural plate cell expressing a patched receptor under conditions sufficient to permit the compound to interact with the neural plate cell; and
   (b) comparing the floor plate cell differentiation of a neural plate cell incubated with the compound with the floor plate cell differentiation of a neural plate cell not incubated with the compound;
   wherein a difference in differentiation of a neural plate cell into a floor plate cell incubated with the compound compared to differentiation of a neural plate cell into a floor plate cell incubated without the compound is indicative of a compound that modulates differentiation of neural plate cells into floor plate cells.

9. The method of claim 8, wherein the hedgehog protein is Sonic hedgehog amino terminal protein.

10. The method of claim 8, wherein the hedgehog protein has the amino acid sequence set forth in SEQ ID NO:12.

11. The method of claim 8, wherein said compound is selected from peptides, peptidomimetics, polypeptides, pharmaceuticals, chemical compounds, biological agents, antibodies, and combinatorial compound libraries.

12. The method of claim 1, wherein differentiation of neural plate cells is compared by comparing expression of HNF3beta.

13. The method of claim 8, wherein differentiation of neural plate cells is compared by comparing expression of HNF3beta.

* * * * *